United States Patent
Vidal et al.

(10) Patent No.: US 6,455,737 B1
(45) Date of Patent: Sep. 24, 2002

(54) CATIONIC A-ACYLAMINOPHENOLS, THEIR USE AS COUPLER FOR OXIDATION DYEING, COMPOSITIONS CONTAINING THEM, AND DYEING METHODS

(75) Inventors: Laurent Vidal; Jean-Baptiste Saunier, both of Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/646,646

(22) PCT Filed: Jan. 21, 2000

(86) PCT No.: PCT/FR00/00143

§ 371 (c)(1),
(2), (4) Date: Nov. 22, 2000

(87) PCT Pub. No.: WO00/43368

PCT Pub. Date: Jul. 27, 2000

(30) Foreign Application Priority Data

Jan. 21, 1999 (FR) .............................. 99 00746

(51) Int. Cl.[7] .............................. C07C 211/00
(52) U.S. Cl. .................... 564/305; 564/48; 564/123
(58) Field of Search ................ 564/305, 48, 123

(56) References Cited

U.S. PATENT DOCUMENTS

| | | | |
|---|---|---|---|
| 3,712,158 A | 1/1973 | Kalopissis et al. | |
| 3,933,913 A | 1/1976 | Colella et al. | |
| 3,961,879 A | 6/1976 | Bugaut et al. | |
| 4,003,699 A | 1/1977 | Rose et al. | |
| 4,044,028 A | 8/1977 | Rosenberger et al. | |
| 4,310,693 A | 1/1982 | Fujita et al. | |
| 4,430,423 A | 2/1984 | Aoki et al. | |
| 4,442,115 A | 4/1984 | Ramsden et al. | |
| 4,772,543 A | 9/1988 | Sato et al. | |
| 4,873,338 A | 10/1989 | Wiesen et al. | |
| 5,061,289 A | 10/1991 | Clausen et al. | |
| 5,380,340 A | 1/1995 | Neunhoeffer et al. | |
| 5,656,569 A | * 8/1997 | Takano et al. ............. | 503/216 |
| 5,766,576 A | 6/1998 | Löwe et al. | |

FOREIGN PATENT DOCUMENTS

| | | | |
|---|---|---|---|
| DE | 1 135 589 | | 8/1962 |
| DE | 23 59 399 | | 6/1975 |
| DE | 28 46 931 | | 5/1979 |
| DE | 30 27 128 | | 2/1981 |
| DE | 32 46 238 | | 6/1983 |
| DE | 34 14 051 | | 10/1984 |
| DE | 36 21 215 | | 1/1988 |
| DE | 253 997 | | 2/1988 |
| DE | 36 41 825 | | 6/1988 |
| DE | 38 43 892 | | 6/1990 |
| DE | 41 33 957 | | 4/1993 |
| DE | 195 43 988 | | 5/1997 |
| EP | 0 065 874 | | 12/1982 |
| EP | 0 079 141 | | 5/1983 |
| EP | 0 081 321 | | 6/1983 |
| EP | 0 115 194 | | 8/1984 |
| EP | 0 168 729 | | 1/1986 |
| EP | 0 193 051 | | 9/1986 |
| EP | 0 579 204 | | 1/1994 |
| EP | 0 608 896 | | 8/1994 |
| EP | 0 790 240 | | 8/1997 |
| FR | 1 596 879 | | 7/1970 |
| FR | 2 140 149 | | 1/1973 |
| FR | 2 233 984 | | 1/1975 |
| FR | 2 275 470 | | 1/1976 |
| FR | 2 733 749 | | 11/1996 |
| GB | 1 026 978 | | 4/1966 |
| GB | 1 153 196 | | 5/1969 |
| GB | 207000 | * | 1/1981 |
| GB | 2 070 000 | | 9/1981 |
| JP | 54-115230 | | 9/1979 |
| JP | 59-59656 | | 4/1984 |
| JP | 62-108859 | | 5/1987 |
| JP | 62-173469 | | 7/1987 |
| JP | 63-208562 | | 8/1988 |
| JP | 64-2045 | | 1/1989 |
| JP | 64-32261 | | 2/1989 |
| JP | 1-249739 | | 10/1989 |
| JP | 2-19576 | | 1/1990 |
| JP | 2-255674 | | 10/1990 |
| JP | 9-110659 | | 4/1997 |
| JP | 9-169705 | | 6/1997 |
| WO | WO 94/08969 | | 4/1994 |
| WO | WO 94/08970 | | 4/1994 |
| WO | WO 94/19316 | | 9/1994 |
| WO | WO 96/15765 | | 5/1996 |
| WO | WO 99/48875 | | 9/1999 |

OTHER PUBLICATIONS

Co–pending application No. 09/646,645; Attorney Docket No. 05725.0769–00000 Title: Compositions for Oxidation Dyeing Keratin Fibres Comprising a Cationic Coupler, Novel Cationic Couplers, Their Use For Oxidation Dyeing and Dyeing Methods Inventor(s): Laurent Vidal et al. U.S. Filing Date: Nov. 21, 2000.

English language Derwent Abstract of DD 253 997, Feb. 10, 1988.

English language Derwent Abstract of DE 34 14 051, Oct. 18, 1984.

English language Derwent Abstract of DE 36 21 215, Jan. 7, 1988.

English language Derwent Abstract of FR 2 140 149, Jan. 12, 1973

(List continued on next page.)

Primary Examiner—Paul J. Killos
Assistant Examiner—Héctor M Reyes
(74) Attorney, Agent, or Firm—Finnegan, Henderson, Farabow, Garrett & Dunner, L.L.P.

(57) ABSTRACT

The invention relates to novel cationic 2-acylaminophenols of formula (I) comprising at least one cationic group, to their use as couplers for the oxidation dyeing of keratin fibers, and in particular of human keratin fibers such as the hair, to oxidation dye compositions containing them in combination with at least one oxidation base, and to oxidation dyeing processes using them.

34 Claims, No Drawings

OTHER PUBLICATIONS

English language Derwent Abstract of FR 2 733 749, Nov. 8, 1996.

English language Derwent Abstract of JP 54–115230, Sep. 7, 1979.

English language Derwent Abstract of JP 62–108859, May 20, 1987.

English language Derwent Abstract of JP 61–173469, Jul. 30, 1987.

English language Derwent Abstract of JP 63–208562, Aug. 30, 1988.

English language Derwent Abstract of JP 64–2045, Jan. 6, 1989.

English language Derwent Abstract of JP 64–32261, Feb. 2, 1989.

English language Derwent Abstract of JP 1–249739, Oct. 5, 1989.

English language Derwent Abstract of JP 2–19576, Jan. 23, 1990.

English language Derwent Abstract of JP 2–255674, Oct. 16, 1990.

English language Derwent Abstract of JP 9–110659, Apr. 28, 1997.

English language Derwent Abstract of JP 9–169705, Jun. 30, 1997.

K. Burdeska, "Über, 4,6–disubstituieret 2–Aminophenole", International Journal of Methods in Synthetic Organic Chemistry, No. 11, Nov. 1982, pp. 940–942.

"Novel Couplers for Use in Colour Photography", Research Disclosure, Feb. 1981, pp. 76–78.

"Preparation and Use as Cyan–Forming Couplers in Silver Halide Colour Photography of 2,5 di–acylaminophenols, Characterized in That the 2–acylaminogroup is Carrying a Tetrahydrofuroylgroup", Research Disclosure, Nov. 1983, pp. 352–353.

"Cyan–forming Phenolic Couplers for Use in Photographic Colour Elements", Research Disclosure, Nov. 1984.

Chemistry & Industry, No. 4, Feb. 17, 1992, pp. 147–151.

Yoshito Abe et al., "A Novel Class of Orally Active Non–Peptide Bradykinin $B_2$ Receptor, Antagonists. 3. Discovering Bioisosteres of the Imidazo[1,2–a]pyridine Moiety", J. Med. Chem. No. 41, 1998, pp. 4062–4079.

* cited by examiner

CATIONIC A-ACYLAMINOPHENOLS, THEIR USE AS COUPLER FOR OXIDATION DYEING, COMPOSITIONS CONTAINING THEM, AND DYEING METHODS

The invention relates to novel cationic 2-acylaminophenols of formula (I) comprising at least one cationic group, to their use as couplers for the oxidation dyeing of keratin fibres, and in particular of human keratin fibres such as the hair, to oxidation dye compositions containing them in combination with at least one oxidation base, and to oxidation dyeing processes using them.

It is known practice to dye keratin fibres, and in particular human hair, with dye compositions containing oxidation dye precursors, in particular ortho-phenylenediamines, para-phenylenediamines, ortho-aminophenols or para-aminophenols and heterocyclic compounds such as diaminopyrazole derivatives, which are generally referred to as oxidation bases. The oxidation dye precursors, or oxidation bases, are colourless or weakly coloured compounds which, when combined with oxidizing products, can give rise to coloured compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colours.

The so-called "permanent" coloration obtained by means of these oxidation dyes must moreover satisfy a certain number of requirements. Thus, it must have no toxicological drawbacks and it must allow shades of the desired intensity to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fibre, which may indeed be differently sensitized (i.e. damaged) between its tip and its root.

4-Aminophenol is generally used to obtain red shades, alone or as a mixture with other bases, and in combination with suitable couplers, and para-phenylenediamines are usually used to obtain blue shades. The use of meta-phenylenediamine-based couplers, in combination with para-phenylenediamine-based couplers usually leads to blue shades whose fastness is generally mediocre.

It has already been proposed, in particular in patent FR-A-1 596 879, to use, for the oxidation dyeing of keratin fibres, phenolic derivatives substituted in position 2 with a ureinyl or thioureinyl radical, in combination with para-phenylenediamine derivatives, in order to obtain shades close to those obtained with meta-phenylenediamine-based couplers. However, dye compositions containing the compounds cited in that patent generally lead on the hair to colours that are too selective and that lack intensity.

Moreover, it has already been proposed, in particular in patent BE 816 674, to use, for the dyeing of keratin fibres, in combination with para-phenylenediamine derivatives, phenolic derivatives substituted in position 2 with an acetyl or ureic radical and in position 5 with a halogen atom, in order to obtain dyeing results ranging from green to green-blue. The light-fastness of the shades obtained on the hair using these compositions are generally better than those obtained with dye compositions containing one or more meta-phenylenediamines as couplers. However, the fastness with respect to bad weather and washing, and the intensities of the colorations obtained are still too low and in these respects constitute major drawbacks for those skilled in the art.

In addition, it has already been proposed, in particular in patent application EP 0 579 204, to use, for the dyeing of keratin fibres, non-cationic phenolic derivatives substituted in position 2 with an acylamino, carbamoyl or ureyl radical, and in position 5 with a $C_1$–$C_4$ alkyl radical, in combination with para-phenylenediamine derivatives. However, the use of the phenolic derivatives cited in that European patent application does not make it possible to obtain a wide range of colours, and furthermore the blue shades generally obtained are not entirely satisfactory as regards their resistance to washing and to the action of light.

The Applicant has now discovered, entirely surprisingly and unexpectedly, that novel 2-acylaminophenols of formula (I) defined below comprising at least one cationic group of formula (II) defined below are not only suitable for use as couplers, but also make it possible to obtain dye compositions which give intense colorations with a wide range of colours, and having excellent properties of resistance with respect to the various treatments to which keratin fibres may be subjected.

These discoveries form the basis of the present invention.

A first subject of the invention is thus novel cationic 2-acylaminophenols of formula (I) below, and the addition salts thereof with an acid:

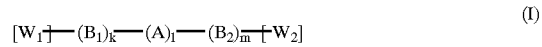

(I)

in which:

the group A represents a group represented by the group D as defined below;

$B_1$ and $B_2$, independently of each other, represent a group represented by the group B as defined below;

k, l and m are integers which can take, independently of each other, the value 0 or 1; the sum k+l+m being non-zero;

$W_1$ and $W_2$ represent, independently of each other, a group W represented by formula (II) below:

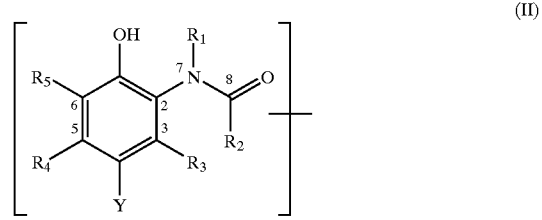

(II)

in which formula (II):

$R_1$ represents a hydrogen atom; a group Z as defined below; a linear or branched radical containing from 1 to 15 carbon atoms (it being possible for the branch(es) to form one or more 3- to 7-membered carbon-based rings) which can contain one or more double bonds and/or one or more triple bonds (the said double bonds optionally leading to aromatic groups), and one or more carbon atoms of which can be replaced with an oxygen, nitrogen or sulphur atom or with an $SO_2$ group, and the carbon atoms of which can, independently of each other, be substituted with one or more halogen atoms; it being understood that the said $SO_2$ group is not directly linked to the nitrogen atom in position 7 bearing the radical $R_1$; the said radical $R_1$ comprising no peroxide linkages or diazo, nitro or nitroso radicals; it being understood that the radical $R_1$ does not represent a hydroxyl, amino, thio, alkoxy or alkylthio radical;

$R_2$ represents a hydrogen atom; a group Z as defined below; a linear or branched radical containing from 1 to 20 carbon atoms (it being possible for the branch(es) to form one or more 3- to 7-membered carbon-based rings) which can contain one or more double bonds and/or one or more triple bonds (the said double bonds optionally leading to aromatic groups), and one or more carbon atoms of which can be replaced with an oxygen, nitrogen or sulphur atom or with an $SO_2$ group, and the carbon atoms of which can, independently of each other, be substituted with one or more halogen atoms; the said radical $R_2$ comprising no peroxide linkages or diazo, nitro or nitroso radicals; and it being understood that $R_2$ cannot represent a hydroxyl or thio radical;

the radicals $R_1$ and $R_2$ can also be linked to form a saturated or unsaturated 5- to 7-membered ring consisting of carbon, nitrogen, oxygen, sulphur and/or of C=O group, each ring member being unsubstituted or substituted with 1 or 2 radicals R, which may be identical or different, R being a linear or branched $C_1$–$C_6$ alkyl radical (it then being possible for the branch(es) to form one or more 3- to 6-membered rings), which can contain one or more double bonds and/or one or more triple bonds (the said double bonds possibly leading to aromatic groups), and one or more carbon atoms of which can be replaced with an oxygen, nitrogen or sulphur atom or with an $SO_2$ group, and the carbon atoms of which can, independently of each other, be substituted with one or more halogen atoms; the said radical R comprising no peroxide linkages or diazo, nitro or nitroso radicals;

$R_3$, $R_4$ and $R_5$, which may be identical or different, represent a hydrogen or halogen atom; a group Z as defined below; a linear or branched radical containing from 1 to 20 carbon atoms (it then being possible for the branch(es) to form one or more 3- to 7-membered rings) which can contain one or more double bonds and/or one or more triple bonds (the said double bonds optionally leading to aromatic groups), and one or more carbon atoms of which can be replaced with an oxygen, nitrogen or sulphur atom or with an $SO_2$ group, and the carbon atoms of which can, independently of each other, be substituted with one or more halogen atoms; the said radicals $R_3$, $R_4$ and $R_5$ comprising no peroxide linkages or diazo, nitro or nitroso radicals; and it being understood that Rs cannot represent a hydroxyl, thio or amino radical or a substituted or unsubstituted sulphonylamino group; and it being understood that the radicals $R_3$, $R_4$ and $R_5$ cannot be linked to the benzene ring of formula (II) via an —NH—NH— linkage;

the radicals $R_1$ and $R_3$ can also be linked to form a saturated 6- to 7-membered ring consisting of carbon, nitrogen, oxygen and sulphur and/or of C=O group, each ring member being unsubstituted or substituted with 1 or 2 radicals R, which may be identical or different, R having the same meanings as those indicated above; the said radical R comprising no peroxide linkages or diazo, nitro or nitroso radicals;

the radicals $R_2$ and $R_3$ can also be linked to form a saturated 5- to 7-membered ring consisting of carbon, nitrogen, oxygen and sulphur and/or of C=O group, each ring member being unsubstituted or substituted with 1 or 2 radicals R, which may be identical or different, R having the same meanings as those indicated above; the said radical R comprising no peroxide linkages or diazo, nitro or nitroso radicals;

Y represents a hydrogen or halogen atom; a group —$OR_6$, —$SR_6$ or —NH—$SO_2R_6$ in which $R_6$ represents a linear or branched $C_1$–$C_6$ alkyl radical (it then being possible for the branch(es) to form one or more 3- to 6-membered rings) unsubstituted or substituted with one or more radicals chosen from the group consisting of a halogen atom, a hydroxyl, $C_1$–$C_4$ alkoxy, amino and $C_1$–$C_4$ aminoalkyl radical; a phenyl radical, unsubstituted or substituted with one or two radicals chosen from the group consisting of a $C_1$–$C_4$ alkyl, trifluoromethyl, carboxyl, ($C_1$–$C_4$) alkoxycarbonyl, halogen, hydroxyl, $C_1$–$C_4$ alkoxy, amino and $C_1$–$C_4$ aminoalkyl radical; or a benzyl radical; and it being understood that Y cannot represent —NH—$SO_2R_6$ when $R_3$ represents a hydroxyl radical;

Z is a cationic group represented by formula (IV) below:

$$—(B)_nD \qquad (IV)$$

in which:

B represents a linear or branched radical containing from 1 to 15 carbon atoms (it then being possible for the branch(es) to form one or more 3- to 7-membered rings) which can contain one or more double bonds and/or one or more triple bonds, the said double bonds optionally leading to aromatic groups, and one or more carbon atoms of which can be replaced with an oxygen, nitrogen or sulphur atom or with an $SO_2$ radical; and one or more carbon atoms of which can, independently of each other, be substituted with one or more halogen atoms or with one or more groups Z; the said radical B comprising no peroxide linkages and no diazo, nitro or nitroso radicals;

D is chosen from the cationic groups of formulae (V) and (VI) below:

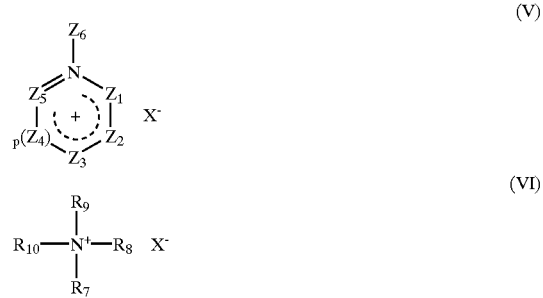

in which:
the radical B is linked to the group D by any one of the atoms in the radical D;

n and p can, independently of each other, take the value 0 or 1;

when n=0, then the group of formula (VI) can be linked to the compound of formula (II) directly via the nitrogen atom of the quaternary ammonium, instead of the radical $R_{10}$;

$Z_1$, $Z_2$, $Z_3$ and $Z_4$, independently of each other, represent an oxygen atom; a sulphur atom; a nitrogen atom which is unsubstituted or substituted with a radical $R_{11}$; or a carbon atom which is unsubstituted or substituted with one or two radicals $R_{11}$, which may be identical or different;

$Z_5$ represents a nitrogen atom; or a carbon atom which is unsubstituted or substituted with a radical $R_{11}$;

$Z_6$ can take the same meanings as those indicated below for the radical $R_{11}$, it being understood that $Z_6$ is other than a hydrogen atom;

in addition, the radicals $Z_1$ or $Z_5$ can form, with $Z_6$, a saturated or unsaturated 5- to 7-membered ring, each ring member being unsubstituted or substituted with one or two radicals $R_{11}$, which may be identical or different;

$R_{11}$ represents a hydrogen atom; a group Z; a linear or branched radical containing from 1 to 10 carbon atoms which can contain one or more double bonds and/or one or more triple bonds, it then being possible for the said double bonds optionally to lead to aromatic groups, and one or more carbon atoms of which can be replaced with an oxygen, nitrogen or sulphur atom or with an $SO_2$ group, and one or more carbon atoms of which can, independently of each other, be substituted with one or more halogen atoms; the said radical comprising no peroxide linkages and no diazo, nitro or nitroso radicals;

two of the adjacent radicals $Z_1$, $Z_2$, $Z_3$, $Z_4$ and $Z_5$ can also form a 5- to 7-membered ring, each ring member being independently represented by a carbon atom which is unsubstituted or substituted with one or two radicals $R_{11}$, which may be identical or different; a nitrogen atom which is unsubstituted or substituted with a radical $R_{11}$; an oxygen atom; or a sulphur atom;

$R_7$, $R_8$, $R_9$ and $R_{10}$, which may be identical or different, have the same meanings as those indicated above for the radical $R_{11}$; the radicals $R_7$, $R_8$ and $R_9$ can also form, in pairs with the quaternary nitrogen atom to which they are attached, one or more saturated 5- to 7-membered rings, each ring member being independently represented by a carbon atom which is unsubstituted or substituted with one or two radicals $R_{11}$, which may be identical or different; a nitrogen atom which is unsubstituted or substituted with a radical $R_{11}$; an oxygen atom; or a sulphur atom;

$x^-$ represents an organic or inorganic anion and is preferably chosen from the group consisting of a halide group such as chloride, bromide, fluoride or iodide; a hydroxide; a sulphate; a hydrogen sulphate; a $(C_1-C_6)$alkyl sulphate such as, for example, a methyl sulphate or an ethyl sulphate; an acetate; a tartrate; an oxalate; a $(C_1-C_6)$alkyl sulphonate such as methyl sulphonate; an aryl sulphonate which is unsubstituted or substituted with a $C_1-C_4$ alkyl radical such as 4-tolyl sulphonate;

it being understood that:

the radical $B_1$ is linked to the group A via any one of the atoms in the radical A;

when k=0, then the group A can be linked to the group $W_1$ directly via the nitrogen atom of the quaternary ammonium, instead of the radical $R_{10}$;

the radical $B_2$ is linked to the group A via any one of the atoms in the radical A;

when m=0, then the group A of formula (VI) can be linked to the group $W_2$ directly via the nitrogen atom of the quaternary ammonium, instead of the radical $R_{10}$;

the group $B_1$ of formula (I) is linked to an atom of the group $W_1$ and this atom is identified by an asterisk (*) on the skeleton of $W_1$ represented by formula (III) defined below;

the group $B_2$ is linked to an atom of the group $W_2$ and this atom is identified by an asterisk (*) on the skeleton of $W_2$ represented by formula (III) defined below;

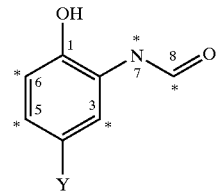

(III)

when k+l=0, then $W_1$ and/or $W_2$ and/or $B_2$ contain at least one group Z when l+m=0, then $W_1$ and/or $W_2$ and/or $B_1$ contain at least one group Z when l=1, then k and m, independently of each other, can take the values 0 and 1.

As mentioned above, the oxidation dye composition containing the compound(s) of formula (I) in accordance with the invention makes it possible to obtain intense colorations in shades ranging from red to blue which furthermore have noteworthy fastness with respect to various treatments to which keratin fibres may be subjected. These properties are particularly noteworthy especially as regards the resistance of the colorations obtained with respect to the action of light, bad weather, washing, permanent-waving and perspiration.

According to the invention, when it is indicated that one or more of the carbon atoms of the radical(s) $R_1$ to $R_5$ can be replaced with an oxygen, nitrogen or sulphur atom or with an $SO_2$ group, and/or when the said radicals $R_1$ to $R_5$ can contain one or more double bonds and/or one or more triple bonds, this means that it is possible, for example, to carry out the following conversions:

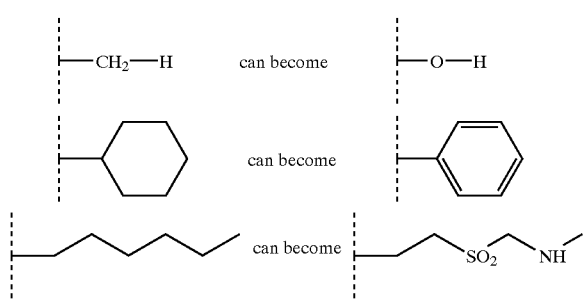

According to the invention, $R_1$ preferably denotes a hydrogen atom, a radical Z or a group $A_1, A_2, A_3, A_4$ or Asp optionally separated from the nitrogen located in position 7, to which the radical $R_1$ is attached, by a —(CO)— group.

According to the invention, the term "group $A_1$" means a linear or branched $C_1$–C alkyl radical, possibly bearing one or two double bonds or one triple bond, possibly being unsubstituted or substituted with a group chosen from a group $A_2$, a group $A_4$ and a group $A_5$, possibly being unsubstituted or substituted with one or two groups, which may be identical or different, chosen from N—$(C_1$–$C_3)$ alkylamino, N—$(C_1$–$C_3)$alkyl-N—$(C_1$–$C_3)$alkylamino, $(C_1$–$C_6)$alkoxy, oxo, alkoxycarbonyl, acyloxy, amide, acylamino, ureyl, sulphoxy, sulphonyl, sulphonamido, sulphonylamino, bromo, cyano and carboxyl groups, and possibly being unsubstituted or substituted with one or more hydroxyl, fluoro or chloro groups.

The term "group $A_2$" means an aromatic group such as phenyl or naphthyl, which may be unsubstituted or substituted with one to three groups, which may be identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl and cyano groups.

The term "group $A_3$" means a heteroaromatic group chosen from furyl, thienyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolyl, benzimidazolyl and benzopyrimidyl groups, the said groups being unsubstituted or substituted with 1 to 3 radicals chosen from linear or branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino or hydroxyl radicals.

The term "group $A_4$" means a $C_3$–$C_7$ cycloalkyl radical, a norbornanyl radical optionally bearing a double bond and unsubstituted or substituted with 1 or 2 radicals defined by linear or branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino and hydroxyl radicals.

The term "group $A_5$" means a heterocycle chosen from dihydrofuryl, tetrahydrofuryl, butyrolactonyl, dihydrothienyl, tetrahydrothienyl, tetrahydrothienonyl, iminothiolane, dihydropyrrolyl, pyrrolidinyl, pyrrolidinonyl, imidazolidinonyl, imidazolidinothienyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridyl, piperidyl, pentalactam, morpholinyl, pyrazoli(di)nyl, pyrimi(di)nyl, pyrazinyl, piperazinyl and azepinyl.

Among these substituents, $R_1$ preferably represents a hydrogen atom; a methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy) benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl or 2-naphthomethyl radical; or a 2-hydroxyethyl, 2-methoxyethyl or 2-ethoxyethyl group.

Even more preferably, $R_1$ represents a hydrogen atom or a methyl radical.

According to the invention, $R_2$ preferably denotes a hydrogen atom or an amino group; a group Z; a group $A_1$, $A_2, A_3, A_4$ or $A_5$ as defined above, optionally separated from the carbon (in position 8) of the amide function of the compound of formula (II) by an —O—, —NH— or —N—$(C_1$–$C_3)$alkyl group.

Among these substituents, $R_2$ preferably denotes a group Z; a radical chosen from the group (G1) consisting of a radical: methyl, ethyl, propyl, isopropyl, butyl, isobutyl, tert-butyl, pentyl, isopentyl, neopentyl, hexyl; cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl; phenyl, methylphenyl, dimethylphenyl, 2,4,6-trimethylphenyl, 4-ethylphenyl, (trifluoromethyl)-phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3,',4'-dimethoxybenzyl, 4'-fluorobenzyl, 4'-chlorobenzyl, phenethyl, 2-phenylvinyl, (1-naphthyl)methyl, (2-naphthyl) methyl; tetrahydrofur-2-yl, fur-2-yl, 5-methyl-2-(trifluoromethyl)fur-3-yl, 2-methyl-5-phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tertbutyl-3-methylpyrazol-5-yl, 3-tertbutyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl; fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane; methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy; amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl, 4-morpholinyl.

When $R_1$ and $R_2$ form a ring, the said ring is referably chosen from 2-pyrrolidinon-1-yl, methyl-2-pyrrolidinon-1-yl, 5-carboxy-2-pyrrolidinon-1-yl, 5-methoxycarbonyl-2-pyrrolidinon-1-yl, pyrazolinon-1-yl, succinimid-1-yl, 3,5-diketopyrazolidin-1-yl, oxindolin-1-yl, maleimid-1-yl, isoindole-1,3-dion-2-yl, 2-piperidinon-1-yl and glutarimid-1-yl groups.

Even more preferably, $R_2$ represents a radical chosen from the group (G2) consisting of a methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl and 4-morpholinyl radical; or a group —$D_1$, —E—$D_1$, —O—E—$D_1$ or —NH—E—$D_1$, in which —E— represents a —$(CH_2)_q$— arm, q being an integer equal to 1 or 2, and $D_1$ represents a group D' chosen from 3-methylimidazolidinium-1-yl, 3-(2-hydroxyethyl)imidazolidinium-1-yl, 1,2,4-triazolinium-1-yl, 1,2,4-triazolinium-4-yl, N—$(C_1-C_4)$alkylpyridinium-2-yl, N—$(C_1-C_4)$alkylpyridinium-3-yl, N—$(C_1-C_4)$alkylpyridinium-4-yl, N-(2-hydroxyethyl)-pyridinium-2-yl, N-(2-hydroxyethyl)pyridinium-3-yl, N-(2-hydroxyethyl)pyridinium-4-yl, pyridinium-1-yl, tri$(C_1-C_4)$alkylammonium-N-yl, 1-methylpiperidinium-1-yl and 1,4-dimethylpiperazinium-1-yl groups.

Even more preferably, $R_2$ represents a methyl, methoxymethyl, 2-carboxyethyl, methoxy, amino, ethylamino or 1-pyrrolidinyl radical; a group —$D_1$, —E—$D_1$, —O—E—$D_1$ or —NH—E—$D_1$, in which —E— represents a —$(CH_2)_q$— arm, q=1 to 2, and $D_1$ represents a group D' as defined above.

According to the invention, $R_3$ and $R_4$, which may be identical or different, preferably denote a hydrogen or halogen atom; a hydroxyl or amino group; a group Z; a group $A_1$ as defined above; a group $A_1, A_2, A_3, A_4$ or $A_5$ as defined above and separated from the phenolic nucleus of formula (II) by an oxygen atom or by an —NH—, —N$(C_1-C_3)$alkyl-, —NH(CO)—, —N$(C_2-C_3)$alkyl-CO—, —NH[C=NH]—, —NH(CO)NH—, —NH(CO)N$(C_1-C_3)$alkyl-, —NH(CO)O—, —NHSO$_2$—, —NHSO$_2$NH— or —NHSO$_2$N$(C_1-C_3)$alkyl-group.

Among these substituents, $R_3$ even more preferably represents a hydrogen or chlorine atom; a group Z; a methyl, hydroxymethyl, methoxymethyl, 1-hydroxyethyl, aminomethyl, methylaminomethyl, hydroxyl, methoxy, amino, methylamino or 2-hydroxyethylamino radical; a group —NH(CO)$R_{12}$ in which $R_{12}$ represents one of the radicals listed in the group (G1) as defined above; a group —NHSO$_2R_{13}$, in which $R_{13}$ represents one of the radicals listed in the group (G3) consisting of methyl, trifluoromethyl, ethyl, 2-chloroethyl, propyl, 3-chloropropyl, isopropyl, butyl, thien-2-yl, hydroxyl, ethoxy and dimethylamino radicals.

When $R_1$ and $R_3$ form a ring, together with the nitrogen atom in position 7 of the compound of formula (II), the preferred linkage for —$R_1R_3$— is —$CH_2CH_2CH_2$—.

When $R_2$ and $R_3$ form a ring, together with the nitrogen atom in position 7 of the compound of formula (II), the preferred linkages for —$R_2R_3$— are —$CH_2$—, —$C(CH_3)_2$— and —$CH_2CH_2$—.

Even more preferably, $R_3$ represents a hydrogen atom; a methyl, hydroxymethyl, aminomethyl, hydroxyl, methoxy, amino or methylamino radical; a methanesulphonylamino group; an ethanesulphonylamino group; a dimethylaminosulphonylamino group; a group —NH(CO)$R_4$ in which $R_{14}$ represents one of the radicals listed in the group (G2) as defined above; or a group —O—E—$D_2$, —NH—E—$D_2$, —NH(CO)—$D_2$, —NH(CO)—E—$D_2$, —NH(CO)O—E—$D_2$, —NH(CO)NH—E—$D_2$, or —NH(SO$_2$)—E—$D_2$, in which —E— has the same meaning as that indicated above and $D_2$ represents a group D' as defined above.

Among these substituents, $R_4$ preferably represents a hydrogen or chlorine atom; a group Z; a methyl, ethyl, hydroxymethyl, methoxymethyl, aminomethyl, methylaminomethyl, hydroxyl, methoxy, acetoxy, amino, methylamino, N-piperidino or N-morpholino radical; a group —NH(CO)$R_{15}$ in which $R_{15}$ represents one of the radicals listed in the group (G1) defined above; or a group —NHSO$_2R_{16}$ in which $R_{16}$ represents one of the radicals listed in the group (G3) defined above.

Even more preferably, $R_4$ represents a hydrogen or chlorine atom; a methyl, hydroxymethyl, aminomethyl, hydroxyl, methoxy, amino or methylamino radical; a methanesulphonylamino group; an ethanesulphonylamino group; a dimethylaminosulphonylamino group; a group —NH(CO)$R_{17}$ in which $R_{17}$ represents one of the radicals listed in the group (G2) defined above; or a group —O—E—$D_3$, —NH—E—$D_3$, —NH(CO)—$D_3$, —NH(CO)—E—$D_3$, —NH(CO)O—E—$D_3$, —NH(CO)NH—E—$D_3$ or —NH(SO$_2$)—E—$D_3$, in which —E— has the same meaning as that given above, and $D_3$ represents a group D' as defined above.

According to the invention, $R_5$ is preferably chosen from a hydrogen or halogen atom; a group Z; a group $A_1$ as defined above; a group $A_1, A_2, A_3, A_4$ or $A_5$ as defined above and separated from the phenolic nucleus of the compounds of formula (II) by an oxygen or sulphur atom or by an —NH—, —N$(C_1-C_3)$alkyl-NH(CO)—, —N$(C_1-C_3)$alkyl(CO)—, —NH[C=NH]—, —NH(CO)NH—, —NH(CO)N$(C_1-C_3)$alkyl- or —NH(CO)O— group.

Among these substituents, $R_5$ preferably represents a hydrogen, chlorine, fluorine or bromine atom; a group Z; a methyl, trifluoromethyl, allyl, methoxy or methylamino radical; or a group —NH(CO)$R_{18}$ in which $R_{18}$ represents one of the radicals listed in the group (G1) defined above.

Even more preferably, $R_5$ represents a hydrogen, chlorine or fluorine atom; a methyl, hydroxymethyl, aminomethyl, methoxy or methylamino radical; a group —NH(CO)$R_{19}$ in which $R_{19}$ represents one of the radicals listed in the group (G2) defined above; or a group —O—E—$D_4$, —NH—E—$D_4$, —NH(CO)—$D_4$, —NH(CO)—E—$D_4$, —NH(CO)O—E—$D_4$ or —NH(CO)NH—E—$D_4$, in which —E— has the same meaning as that given above, and $D_4$ represents a group D' as defined above.

According to the invention, Y is preferably chosen from a hydrogen, chlorine, fluorine or bromine atom; a methoxy, ethoxy, propoxy, benzyloxy or phenoxy group; or an —OCH$_2$CH$_2$OCH$_3$, —OCH$_2$CH$_2$OCH$_3$, —OCH$_2$CH$_2$N(CH$_3$)$_2$, —OCH$_2$(CO)OH, —OCH$_2$(CO)OCH$_3$, —OCH$_2$(CO)OC$_2$H$_5$, —SCH$_2$CH$_2$CO$_2$H or —NHSO$_2$CH$_3$ group; it being understood that Y cannot represent an —NHSO$_2$CH$_3$ group when $R_3$ represents a hydroxyl radical.

Even more preferably, Y represents a hydrogen or chlorine atom; or a methoxy, —OCH$_2$(CO)OH or —OCH$_2$(CO)OCH$_3$ group.

Among the groups D which may be mentioned, for example, are imidazolinium, thiazolinium, oxazolinium, pyrrolinium, 1,2,3-triazolinium, 1,2,4-triazolinium, isoxazolinium, isothiazolinium, imidazolidinium, thiazolidinium, pyrazolinium, pyrazolidinium, oxazolidinium, pyrazoltriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, $(C_1-C_4)$ tetraalkylammonium, polyhydroxy $(C_1-C_4)$ tetraalkylammonium, dialkylpiperidinium, dialkylpyrrolidinium, dialkylmorpholinium, dialkylthiomorpholinium, dialkylpiperazinium, azepinium and 1,4-diazabicyclo[2,2,2]octanium groups.

Even more preferably, D represents a 3-methylimidazolidinium-1-yl, 3-(2-hydroxyethyl) imidazolidinium-1-yl, 1,2,4-triazolinium-1-yl, 1,2,4-triazolinium-4-yl, N—$(C_1-C_4)$alkylpyridinium-2-yl, N—$(C_1-C_4)$alkylpyridinium-3-yl, N—$(C_1-C_4)$alkylpyridinium-4-yl, N-(2-hydroxyethyl)pyridinium-2-yl, N-(2-hydroxyethyl)pyridinium-3-yl, N-(2-hydroxyethyl)pyridinium-4-yl, pyridinium-1-yl, $(C_1-C_4)$trialkylammonium-N-yl, 1-methylpiperidinium-1-yl or 1,4-dimethylpiperazinium-1-yl group.

A preferably represents an imidazolidinium, N—$(C_1-C_4)$alkylpyridinium, N-(2-hydroxyethyl)pyridinium, pyridinium, di$(C_1-C_4)$alkylammonium or 1,4-dimethylpiperazinium-1-yl group.

Preferably, B, $B_1$ and $B_2$, independently of each other, represent a —$(CH_2)$—, —$(CH_2)$—$(CH_2)$— or —$(CH_2)$—$(CH_2)$—$(CH_2)$— arm.

Among the compounds of formula (I) above which may be mentioned most particularly are:

1,3-bis[(2-hydroxyphenylcarbamoyl)methyl]-3H-imidazol-1-ium chloride;
1,3-bis[(2-hydroxy-4-methylphenylcarbamoyl)methyl]-3H-imidazol-1-ium chloride;
1,3-bis[(2-hydroxy-4-aminophenylcarbamoyl)methyl]-3H-imidazol-1-ium chloride;
1,3-bis[(2-hydroxy-4-acetylaminophenylcarbamoyl)methyl]-3H-imidazol-1-ium chloride;
1,3-bis[(2-hydroxy-4-methoxycarbonylaminophenylcarbamoyl)methyl]-3H-imidazol-1-ium chloride;
1,3-bis[(3-hydroxy-4-acetylaminophenylcarbamoyl)methyl]-3H-imidazol-1-ium chloride;
1,3-bis[(3-hydroxy-4-methoxycarbonylaminophenylcarbamoyl)methyl]-3H-imidazol-1-ium chloride;
1,3-bis[(2-hydroxy-5-chlorophenylcarbamoyl)methyl]-3H-imidazol-1-ium chloride;
1,3-bis[(2-hydroxy-4-methyl-5-chlorophenylcarbamoyl)methyl]-3H-imidazol-1-ium chloride;
1,3-bis[(2-hydroxy-4-amino-5-chlorophenylcarbamoyl)methyl]-3H-imidazol-1-ium chloride;
1,3-bis[(2-hydroxy-4-acetylamino-5-chlorophenylcarbamoyl)methyl]-3H-imidazol-1-ium chloride;
1,3-bis[(2-hydroxy-4-methoxycarbonylamino-5-chlorophenylcarbamoyl)methyl]-3H-imidazol-1-ium chloride;
1,3-bis[(3-hydroxy-4-acetylamino-5-chlorophenylcarbamoyl)methyl]-3H-imidazol-1-ium chloride;
1,3-bis[(3-hydroxy-4-methoxycarbonylamino-6-chlorophenylcarbamoyl)methyl]-3H-imidazol-1-ium chloride;
1,3-bis[(2-hydroxy-5-methoxyphenylcarbamoyl)methyl]-3H-imidazol-1-ium chloride;
1,3-bis[(2-hydroxy-4-methyl-5-methoxyphenylcarbamoyl)methyl]-3H-imidazol-1-ium chloride;
1,3-bis[(2-hydroxy-4-amino-5-methoxyphenylcarbamoyl)methyl]-3H-imidazol-1-ium chloride;
1,3-bis[(2-hydroxy-4-acetylamino-5-methoxyphenylcarbamoyl)methyl]-3H-imidazol-1-ium chloride;
1,3-bis[(2-hydroxy-4-methoxycarbonylamino-5-methoxyphenylcarbamoyl)methyl]-3H-imidazol-1-ium chloride;
1,3-bis[(3-hydroxy-4-acetylamino-6-methoxyphenylcarbamoyl)methyl]-3H-imidazol-1-ium chloride;
1,3-bis[(3-hydroxy-4-methoxycarbonylamino-6-methoxyphenylcarbamoyl)methyl]-3H-imidazol-1-ium chloride;
1,3-bis[(2-hydroxy-6-aminophenylcarbamoyl)methyl]-3H-imidazol-1-ium chloride;
1,3-bis[(2-hydroxy-6-acetylaminophenylcarbamoyl)methyl]-3H-imidazol-1-ium chloride;
1,3-bis[(2-hydroxy-4,6-diaminophenylcarbamoyl)methyl]-3H-imidazol-1-ium chloride;
1,3-bis[(2-hydroxy-4-acetylamino-6-aminophenylcarbamoyl)methyl]-3H-imidazol-1-ium chloride;
1,3-bis[(2-hydroxy-3,5-dichloro-4-methylphenylcarbamoyl)methyl]-3H-imidazol-1-ium chloride;
1,3-bis[(2-hydroxy-3,5-dichloro-4-aminophenylcarbamoyl)methyl]-3H-imidazol-1-ium chloride;
1,3-bis[(2-hydroxy-3,5-dichloro-4-acetylaminophenylcarbamoyl)methyl]-3H-imidazol-1-ium chloride;
1,3-bis[(2-hydroxy-3,5-dichloro-4-methoxycarbonylaminophenylcarbamoyl)methyl]-3H-imidazol-1-ium chloride;
1,3-bis[(2-hydroxy-3-acetylaminophenylcarbamoyl)methyl]-3H-imidazol-1-ium chloride;
3-[(2-hydroxy-4-aminophenylcarbamoyl)methyl]-1-[(2-hydroxy-4-methylphenylcarbamoyl)methyl]-3H-imidazol-1-ium chloride;
3-[(2-hydroxy-3,5-dichloro-4-methylphenylcarbamoyl)methyl]-1-[(2-hydroxy-4-methylphenylcarbamoyl)methyl]-3H-imidazol-1-ium chloride;
1,4-bis[(2-hydroxyphenylcarbamoyl)methyl]-1-methylpiperazin-1-ium chloride;
1,4-bis[(2-hydroxy-4-methylphenylcarbamoyl)methyl]-1-methylpiperazin-1-ium chloride;
1,4-bis[(2-hydroxy-4-aminophenylcarbamoyl)methyl]-1-methylpiperazin-1-ium chloride;
1,4-bis[(2-hydroxy-4-acetylaminophenylcarbamoyl)methyl]-1-methylpiperazin-1-ium chloride;
1,4-bis[(2-hydroxy-4-methoxycarbonylaminophenylcarbamoyl)methyl]-1-methylpiperazin-1-ium chloride;
1,4-bis[(3-hydroxy-4-acetylaminophenylcarbamoyl)methyl]-1-methylpiperazin-1-ium chloride;
1,4-bis[(3-hydroxy-4-methoxycarbonylaminophenylcarbamoyl)methyl]-1-methylpiperazin-1-ium chloride;
1,4-bis[(2-hydroxy-5-chlorophenylcarbamoyl)methyl]-1-methylpiperazin-1-ium chloride;
1,4-bis[(2-hydroxy-4-methyl-5-chlorophenylcarbamoyl)methyl]-methylpiperazin-1-ium chloride;
1,4-bis[(2-hydroxy-4-amino-5-chlorophenylcarbamoyl)methyl]-1-methylpiperazin-1-ium chloride;

1,4-bis[(2-hydroxy-4-acetylamino-5-chlorophenylcarbamoyl)methyl]-1-methylpiperazin-1-ium chloride;
1,4-bis[(2-hydroxy-4-methoxycarbonylamino-5-chlorophenylcarbamoyl)methyl]-1-methylpiperazin-1-ium chloride;
1,4-bis[(3-hydroxy-4-acetylamino-6-chlorophenylcarbamoyl)methyl]-1-methylpiperazin-1-ium chloride;
1,4-bis[(3-hydroxy-4-methoxycarbonylamino-6-chlorophenylcarbamoyl)methyl]-1-methylpiperazin-1-ium chloride;
1,4-bis[(2-hydroxy-5-methoxyphenylcarbamoyl)methyl]-1-methylpiperazin-1-ium chloride;
1,4-bis[(2-hydroxy-4-methyl-5-methoxyphenylcarbamoyl)methyl]-1-methylpiperazin-1-ium chloride;
1,4-bis[(2-hydroxy-4-amino-5-methoxyphenylcarbamoyl)methyl]-1-methylpiperazin-1-ium chloride;
1,4-bis[(2-hydroxy-4-acetylamino-5-methoxyphenylcarbamoyl)methyl]-1-methylpiperazin-1-ium chloride;
1,4-bis[(2-hydroxy-4-methoxycarbonylamino-5-methoxyphenylcarbamoyl)methyl]-1-methylpiperazin-1-ium chloride;
1,4-bis[(3-hydroxy-4-acetylamino-6-methoxyphenylcarbamoyl)methyl]-1-methylpiperazin-1-ium chloride;
1,4-bis[(3-hydroxy-4-methoxycarbonylamino-6-methoxyphenylcarbamoyl)methyl]-1-methylpiperazin-1-ium chloride;
1,4-bis[(2-hydroxy-6-aminophenylcarbamoyl)methyl]-1-methylpiperazin-1-ium chloride;
1,4-bis[(2-hydroxy-6-acetylaminophenylcarbamoyl)methyl]-1-methylpiperazin-1-ium chloride;
1,4-bis[(2-hydroxy-4,6-diaminophenylcarbamoyl)methyl]-1-methylpiperazin-1-ium chloride;
1,4-bis[(2-hydroxy-4-acetylamino-6-aminophenylcarbamoyl)methyl]-1-methylpiperazin-1-ium chloride;
1,4-bis[(2-hydroxy-3,5-dichloro-4-methylphenylcarbamoyl)methyl]-1-methylpiperazin-1-ium chloride;
1,4-bis[(2-hydroxy-3,5-dichloro-4-aminophenylcarbamoyl)methyl]-1-methylpiperazin-1-ium chloride;
1,4-bis[(2-hydroxy-3,5-dichloro-4-acetylaminophenylcarbamoyl)methyl]-1-methylpiperazin-1-ium chloride;
1,4-bis[(2-hydroxy-3,5-dichloro-4-methoxycarbonylaminophenylcarbamoyl)methyl]-1-methylpiperazin-1-ium chloride;
1,4-bis[(2-hydroxy-3-acetylaminophenylcarbamoyl)methyl]-1-methylpiperazin-1-ium chloride;

and the addition salts thereof with an acid.

The compounds of formula (I) in accordance with the invention can be prepared according to methods that are well known in the prior art and are described, for example, in patents and patent applications FR-A-1 596 879; BE 816 674; EP 0 579 204; DE 2 846 931; JP- 54-115 230; GB 2 070 000; DE 3 027 128; EP 0 065 874; EP 0 115 194; EP 0 079 141; EP 0 081 321; DE 3 246 238; EP 0 168 729; DE 3 414 051; JP-59-059 656; FR-A-2 575 470; EP 0 193 051; JP-63-208 562; JP-62-173 469; JP-62-108 859; JP-62-173 469; DD 253 997; DE 3 641 825, JP-63-208 562; DE 3 621 215; JP-01-249 739; JP-64-002 045; JP-02-255 674; JP-01-032 261; JP-02-255 674; EP 0 608 896; WO 94/19316; JP-09-169 705; EP 0 790 240; as well as in the documents Res. Discl. (1981), 202, 76–8; Synthesis (1982), 940–2; Res. Discl. (1983), 235, 352–3; Res. Discl. (1984), 247, 554–6, Res. Discl. (1985), 251, 134–9; Chem. Ind. (Dekker) (1992), 47 (Catal. Org. React.), 147–51; and J. Med. Chem. (1998), 41, 4062–79.

Another subject of the invention is the use of the compounds of formula (I) in accordance with the invention as couplers for the oxidation dyeing of keratin fibres, and in particular of human keratin fibres such as the hair.

The invention also relates to a composition for the oxidation dyeing of keratin fibres, and in particular of human keratin fibres such as the hair, characterized in that it comprises, in a medium which is suitable for dyeing, at least one compound of formula (I) in accordance with the invention and at least one oxidation base.

The compound(s) of formula (I) in accordance with the invention and/or the addition salt(s) thereof with an acid preferably represent(s) from 0.0005 to 12% by weight approximately relative to the total weight of the dye composition, and even more preferably from 0.005 to 6% by weight approximately relative to this weight.

The nature of the oxidation base(s) which can be used in the dye composition in accordance with the invention is not critical. They are preferably chosen from the oxidation bases conventionally used in oxidation dyeing, among which mention may be made in particular of para-phenylenediamines, bis(phenyl)alkylenediamines, para-aminophenols, ortho-aminophenols and heterocyclic bases.

Among the para-phenylenediamines which can be mentioned more particularly, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(O-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine and N-(β-methoxyethyl)-para-phenylenediamine, and the addition salts thereof with an acid.

Among the para-phenylenediamines mentioned above, the ones most particularly preferred are para-phenylenediamine, para-tolylenediamine, 2-isopropyl-para-phenylenediamine, 2-β-hydroxyethyl-para-phenylenediamine, 2-hydroxyethyloxy-para-phenylenediamine, 2,6-dimethyl -para-phenylenediamine, 2,6-diethyl-para-phenylenediamine, 2,3-dimethyl-para-phenylenediamine, N,N-bis(β-hydroxyethyl)-para-phenylenediamine, 2,-chloro-para-phenylenediamine and 2-β-acetylaminoethyl oxy-para-phenylenediamine, and the addition salts thereof with an acid.

Among the bis(phenyl)alkylenediamines which can be mentioned more particularly, for example, are N,N'-bis(β-hydroxyethyl)-N,N'-bis(4'-aminophenyl)-1,3-diaminopropanol, N,N'-bis(β-hydroxyethyl)-N,N'-bis(4'- aminophenyl)ethylenediamine, N,N'-bis(4-aminophenyl)-tetramethylenediamine, N,N'-bis(P-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)-ethylenediamine and 1,8-bis(2,5-diaminophenoxy)-3,5-dioxaoctane, and the addition salts thereof with an acid.

Among the para-aminophenols which can be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols which can be mentioned more particularly, for example, are 2-aminophenol, 2-amino-5-methylphenol, 2-amino-6-methylphenol and 5-acetamido-2-aminophenol, and the addition salts thereof with an acid.

Among the heterocyclic bases which can be mentioned more particularly, for example, are pyridine derivatives, pyrimidine derivatives and pyrazole derivatives.

Among the pyridine derivatives which may be mentioned more particularly are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives which may be mentioned more particularly are the compounds described, for example, in German patent DE 2 359 399 or Japanese patents JP 88-169 571 and JP 91-10659 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol, 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine and 2,5,N7,N7-tetramethylpyrazolo[1,5-a]pyrimidine-3,7-diamine, and the addition salts thereof and the tautomeric forms thereof, when a tautomeric equilibrium exists, and the addition salts thereof with an acid.

Among the pyrazole derivatives which may be mentioned more particularly are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

According to the invention, the dye compositions containing one or more para-phenylenediamines and/or one or more heterocyclic oxidation bases are particularly preferred.

The oxidation base(s) preferably represent(s) from 0.0005% to 12% by weight approximately relative to the total weight of the dye composition, and even more preferably from 0.005% to 6% by weight approximately relative to this weight.

In addition to the compound(s) of formula (I) above, the dye composition in accordance with the invention can also include one or more additional couplers which can be chosen from the couplers used conventionally in oxidation dyeing and among which mention may be made in particular of meta-phenylenediamines, meta-aminophenols, meta-diphenols and heterocyclic couplers such as, for example, indole derivatives, indolene derivatives, pyridine derivatives and pyrazolones, and the addition salts thereof with an acid.

These couplers are chosen more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, a-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one and 1-phenyl-3-methylpyrazol-5-one, and the addition salts thereof with an acid.

When they are present, these couplers preferably represent from 0.0001 to 10% by weight approximately relative to the total weight of the dye composition and even more preferably from 0.005 to 5% by weight approximately relative to this weight.

In general, the addition salts with an acid which can be used in the context of the dye compositions of the invention (compounds of formula (I), additional oxidation bases and couplers) are chosen in particular from the hydrochlorides, hydrobromides, sulphates, citrates, succinates, tartrates, lactates and acetates.

The medium which is suitable for dyeing (or the support) generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12 approximately, and preferably between 5 and 11 approximately. It can be adjusted to the desired value using acidifying or basifying agents commonly used to dye keratin fibres.

Among the acidifying agents which may be mentioned, for example, are inorganic or organic acids such as hydrochloric acid, orthophosphoric acid, sulphuric acid, carboxylic acids such as acetic acid, tartaric acid, citric acid and lactic acid, and sulphonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (V) below:

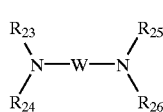

(V)

in which W is a propylene residue optionally substituted with a hydroxyl group or a $C_1$–$C_6$ alkyl radical; $R_{23}$, $R_{24}$, $R_{25}$ and $R_{26}$, which may be identical or different, represent a hydrogen atom, a $C_1$–$C_6$ alkyl radical or a $C_1$–$C_6$ hydroxyalkyl radical.

The oxidation dye compositions in accordance with the invention can also include at least one direct dye, in particular in order to modify the shades or to enrich them with glints.

The dye composition in accordance with the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The dye composition according to the invention can be in various forms, such as in the form of liquids, creams or gels or in any other form which is suitable for dyeing keratin fibres, and in particular human hair.

The invention also relates to a process for dyeing keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition just at the time of use, or which is present in an oxidizing composition which is applied simultaneously or sequentially.

According to one preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibres and is left in place for 3 to 50 minutes approximately, preferably 5 to 30 minutes approximately, after which the fibres are rinsed, washed with shampoo, rinsed again and dried.

The oxidizing agent can be chosen from the oxidizing agents conventionally used for the oxidation dyeing of keratin fibres, and among which mention may be made of hydrogen peroxide, urea peroxide, alkali metal bromates, persalts such as perborates and persulphates, and enzymes such as peroxidases, laccases, tyrosinases and oxidoreductases among which mention may be made in particular of pyranose oxidases, glucose oxidases, glycerol oxidases, lactate oxidases, pyruvate oxidases and uricases.

The pH of the oxidizing composition containing the oxidizing agent as defined above is such that, after mixing with the dye composition, the pH of the resultant composition applied to the keratin fibres preferably varies between 3 and 12 approximately, and even more preferably between 5 and 11. It is adjusted to the desired value using acidifying or basifying agents commonly used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams, gels or any other form which is suitable for dyeing keratin fibres, and in particular human hair.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with a means for delivering the desired mixture onto the hair, such as the devices described in patent FR 2,586,913 in the name of the Applicant.

The examples which follow are intended to illustrate the invention.

PREPARATION EXAMPLE

Synthesis of 1,3-bis[(2-hydroxy-4-methylphenylcarbamoyl)methyl]-3H-imidazol-1-ium chloride

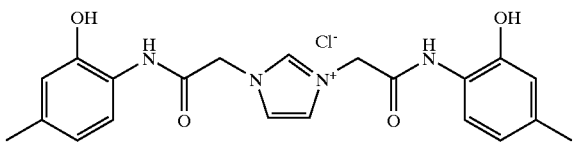

a) Preparation of 2-chloro-N-(2-hydroxy-4-methylphenyl)acetamide 95 ml of triethylamine (0.674 mol) were added to a solution of 83 g of 2-hydroxy-4-methylaniline (0.674 mol) in 2.5 liters of tetrahydrofuran, with stirring and under an inert atmosphere, followed, after 30 minutes, by dropwise addition of a solution of 54 ml of chloroacetyl chloride (0.678 mol) in 60 ml of tetrahydrofuran, while maintaining the temperature at 25–27° C. The reaction medium was stirred at room temperature for 4 hours, filtered through a sinter funnel and the inorganic salts were rinsed with 500 ml of tetrahydrofuran. The combined organic phases were poured into 3 liters of ice-cold water with stirring. The precipitate formed was spin-filtered, washed with twice 600 ml of water and once with pentane, and dried under vacuum to constant weight, to give 99 g of 2-chloro-N-(2-hydroxy-4-methylphenyl)acetamide in the form of a beige-coloured powder, in a yield of 74%.

b) Preparation of 1,3-bis[(2-hydroxy-4-methylphenylcarbamoyl)methyl]-3H-imidazol-1-ium chloride A solution of 2-chloro-N-(2-hydroxy-4-methylphenyl)acetamide (6 g, 30 mmol) obtained above in the preceding step, and imidazole (680 mg, 10 mmol) in 40 ml of 1,2-dimethoxyethylene was refluxed for 48 hours. The precipitate formed was spin-filtered and washed twice with 1,2-dimethoxyethylene. The 2 g of white powder thus obtained were suspended in 100 ml of water. The pH of the reaction medium was brought to 7.0 by addition of sodium hydroxide solution (10% and then 0.1%). The precipitate was spin-filtered and washed with the minimum amount of water, and then stirred for one hour in 800 ml of water. The suspension was filtered. The aqueous filtrate was concentrated under vacuum and dried under vacuum to constant weight, to give 0.5 g of 1,3-bis[(2-hydroxy-4-methylphenylcarbamoyl)methyl]-3H-imidazol-1-ium chloride in the form of a white powder melting at 232° C., and the cation mass spectroscopy: m/z=395 was in accordance with the expected product.

DYEING EXAMPLES

Examples 1 to 3 of Dyeing of an Alkaline Medium

The dye compositions below were prepared (contents in grams):

| EXAMPLE | 1 | 2 | 3 |
|---|---|---|---|
| 1,3-Bis[(2-hydroxy-4-methylphenylcarbamoyl)methyl]-3H-imidazol-1-ium chloride (compound of formula (I)) | 1.30 | 1.30 | 1.30 |
| para-Phenylenediamine (oxidation base) | 0.324 | — | — |
| Pyrazolo[1,5-a]pyrimidine-3,7-diamine dihydrochloride (oxidation base) | — | 0.666 | — |
| N,N-Bis(hydroxyethyl)-para-phenylenediamine dihydrochloride (oxidation base) | — | — | 0.882 |
| Common dye support No. 1 | (*) | (*) | (*) |
| Demineralized water qs | 100 g | 100 g | 100 g |

(*) Common dye support No. 1:
Benzyl alcohol 2.0 g
Polyethylene glycol containing 6 mol of ethylene oxide 3.0 g
96° ethanol 20.0 g
($C_8$–$C_{10}$)Alkylpolyglucoside as an aqueous solution containing 60% active material (A.M.), buffered with ammonium citrate, sold under the name Oramix CG 110 ® by the company SEPPIC 6.0 g
Aqueous ammonia containing 20% $NH_3$ 10.0 g
Sodium metabisulphite containing 35% active material 0.228 g
Pentasodium salt of diethylene-triaminepentaacetic acid 1.1 g At the time of use, each of the dye compositions above was mixed weight for weight with a 20-volumes hydrogen peroxide solution (6% by weight) of pH 3.

The mixture obtained was applied to locks of natural grey hair containing 90% white hairs, for 30 minutes. The locks were then rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | Slightly bluish ashen light-chestnut |
| 2 | 10 ± 0.2 | Iridescent blond |
| 3 | 10 ± 0.2 | Matt blue |

What is claimed is:
1. A composition for the oxidation dyeing of keratin fibres comprising in a medium which is suitable for dyeing:
at least one oxidation base, and
at least one coupler chosen from a cationic 2-acylaminophenol of formula (I) below or an acid addition salt thereof:

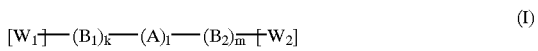

(I)

wherein:
A is a group chosen from a group D as defined below;
$B_1$ and $B_2$, independently, are each chosen from a group B as defined below;
k, l, and m, independently, are each integers having a value chosen from 0 and 1, wherein the sum k+l+m is not equal to zero;
$W_1$ and $W_2$, independently, are each chosen from a group W, wherein said group W is a group of formula (II) below:

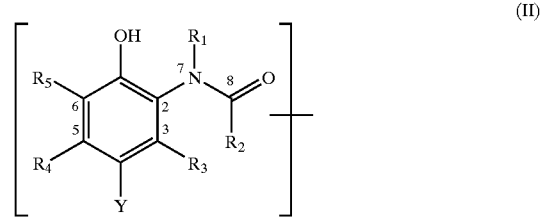

(II)

wherein:
$R_1$ is chosen from a hydrogen atom; a group Z as defined below; and linear and branched radicals comprising from 1 to 15 carbon atoms, wherein:
said branched radicals may form at least one carbon-based ring comprising from 3 to 7 ring members,
said linear and branched radicals may comprise at least one double bond and/or at least one triple bond, wherein double bonds optionally lead to an aromatic group,
at least one carbon atom of said linear and branched radicals, independently, may be replaced with a replacement chosen from oxygen, nitrogen, and sulphur atoms, and a $SO_2$ group, and
said carbon atoms of said linear and branched radicals may, independently, be substituted with at least one halogen atom,
with the provisos that the nitrogen atom in position 7 carrying $R_1$ is not linked directly to said $SO_2$ group; $R_1$ comprises no linkage chosen from peroxide linkages and no radicals chosen from diazo, nitro, and nitroso radicals; and R1 is not chosen from hydroxyl, amino, thio, alkoxy, and alkylthio radicals;

$R_2$ is chosen from a hydrogen atom; a group Z as defined below; and linear and branched radicals comprising from 1 to 20 carbon atoms, wherein:
said branched radicals may form at least one carbon-based ring comprising from 3 to 7 ring members,
said linear and branched radicals may comprise at least one double bond and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group, and
said carbon atoms of said linear and branched radicals, independently, may be substituted with at least one halogen,
with the provisos that $R_2$ comprises no linkage chosen from peroxide linkages and no radicals chosen from diazo, nitro, and nitroso radicals, and $R_2$ is not chosen from hydroxyl and thio groups;
$R_1$ and $R_2$ may be linked together to form a ring comprising from 5 to 7 ring members, wherein:
said ring is saturated or unsaturated,
said ring members, independently, are each chosen from carbon, nitrogen, oxygen, and sulphur atoms, and a C=O group,
said ring members, independently, are each unsubstituted or substituted with from 1 to 2 radicals chosen from R, R being chosen from linear and branched $C_1$–$C_6$ alkyl radicals, wherein:
said linear and branched $C_1$–$C_6$ alkyl radicals may form at least one ring comprising from 3 to 6 ring members,
said linear and branched $C_1$–$C_6$ alkyl radicals may form at least one double and/or at least one triple bond, wherein double bonds optionally lead to an aromatic group,
at least one carbon atom of said linear and branched $C_1$–$C_6$ alkyl radicals, independently, may be replaced with a replacement chosen from oxygen, nitrogen, and sulphur atoms, and an $SO_2$ group,
the carbon atoms of said linear and branched $C_1$–$C_6$ alkyl radicals, independently, may be substituted with at least one halogen atom, and
with the proviso that R comprises no linkage chosen from peroxide linkages and no radicals chosen from diazo, nitro, and nitroso radicals;
$R_3$, $R_4$, and $R_5$, which are identical or different, are each chosen from hydrogen and halogen atoms; a group Z as defined below; and linear and branched radicals comprising from 1 to 20 carbon atoms, wherein:
said linear and branched radicals may form at least one ring comprising from 3 to 7 ring members,
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group, and
the carbon atoms of said linear and branched radicals, independently, may be substituted with at least one halogen atom,
with the provisos that $R_3$, $R_4$, and $R_5$ comprise no linkage chosen from peroxide linkages and no radicals chosen from diazo, nitro, and nitroso radicals; $R_5$ is not chosen from hydroxyl, thio, and amino groups, and substituted and unsubstituted sulphonylamino groups; and $R_3$, $R_4$, and $R_5$ are not linked to the benzene ring of formula (II) via an —NH—NH— linkage;
$R_1$ and $R_3$ are optionally linked together to form a saturated ring comprising from 6 to 7 ring members, wherein:
said ring members, independently, are each chosen from carbon, nitrogen, oxygen, and sulphur atoms, and a C=O group, and
said ring members, independently, are each unsubstituted or substituted with from 1 to 2 substituents, which may be the same or different, chosen from R, wherein R is defined above;
$R_2$ and $R_3$ are optionally linked together to form a saturated ring comprising from 5 to 7 ring members, wherein:
said ring members, independently, are each chosen from carbon, nitrogen, oxygen, and sulphur atoms, and a C=O group, and
said ring members, independently, are each unsubstituted or substituted with from 1 to 2 substituents, which may be identical or different, chosen from R, wherein R is defined above;
Y is chosen from hydrogen and halogen atoms; and —$OR_6$, —$SR_6$, and —NH—$SO_2R_6$ groups, wherein:
$R_6$ is chosen from linear and branched $C_1$–$C_6$ alkyl radicals,
said branched $C_1$–$C_6$ alkyl radicals may form at least one ring comprising from 3 to 6 ring members,
said linear and branched $C_1$–$C_6$ alkyl radicals are unsubstituted or substituted with at least one group chosen from a halogen atom; hydroxyl, $C_1$–$C_4$ alkoxy, amino, and $C_1$–$C_4$ aminoalkyl groups; a benzyl group; and a phenyl radical,
wherein said phenyl radical is unsubstituted or substituted with one or two substituents, which may be identical or different, chosen from $C_1$–$C_4$ alkyl, trifluoromethyl, carboxyl, ($C_1$–$C_4$)alkoxycarbonyl, halogen, hydroxyl, $C_1$–$C_4$ alkoxy, amino, and $C_1$–$C_4$ aminoalkyl groups; and
with the proviso that Y is not chosen from —NH—$SO_2R_6$ when $R_3$ is a hydroxyl group; and
Z is a cationic group of formula (IV):

$$-(B)_n-D \qquad (IV)$$

wherein:
B is chosen from linear and branched radicals comprising from 1 to 15 carbon atoms, wherein
said branched radicals may form at least one ring comprising from 3 to 7 ring members,
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group, and
the carbon atoms of said linear and branched radicals, independently, may be substituted with at least one substituent chosen from halogen atoms and a group Z; and with the proviso that B comprises no linkage chosen from peroxide linkages and no radicals chosen from diazo, nitro, and nitroso radicals; and D is chosen from the cationic groups of formulae (V) and (VI):

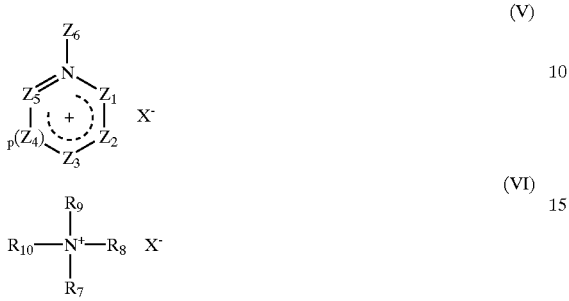

wherein:
B is linked to the radical D by any atom in the radical D, n and p, independently, each have a value chosen from 0 and 1, when n=0, the group of formula (VI) can be linked to the compound of formula (II) directly via the nitrogen atom of the quaternary ammonium, in place of the radical $R_{10}$;

$Z_1$, $Z_2$, $Z_3$, and $Z_4$, independently, are each chosen from oxygen and sulphur atoms, nitrogen atoms which are unsubstituted or substituted with a substituent chosen from $R_{11}$, and carbon atoms which are unsubstituted or substituted with one or two substituents, which may be identical or different, chosen from $R_{11}$;

$Z_5$ is chosen from a nitrogen atom, and carbon atoms which are unsubstituted or substituted with a substituent chosen from $R_{11}$;

$Z_6$ is chosen from $R_{11}$, with the proviso that $Z_6$ is not a hydrogen atom;

$Z_6$ may form, with one of $Z_1$ and $Z_5$, a saturated or unsaturated ring comprising from 5 to 7 ring members, each ring member being unsubstituted or substituted with one or two substituents, which may be identical or different, chosen from $R_{11}$;

$R_{11}$ is chosen from a hydrogen atom; group Z; and linear and branched radicals comprising from 1 to 10 carbon atoms, wherein
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group,
the carbon atoms of said linear and branched radicals, independently, may be substituted with at least one halogen, and
with the proviso that said linear and branched radicals comprise no linkages chosen from peroxide linkages and no radicals chosen from diazo, nitro, and nitroso radicals;

adjacent pairs of radicals chosen from $Z_1$, $Z_2$, $Z_3$, $Z_4$, and $Z_5$ can optionally form a ring comprising from 5 to 7 ring members, wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms;

$R_7$, $R_8$, $R_9$, and $R_{10}$, which may be identical or different, are each chosen from $R_{11}$;

$R_7$, $R_8$, and $R_9$ may also form, in pairs with the quaternary nitrogen atom to which they are attached, at least one saturated ring comprising from 5 to 7 ring members,
wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms; and $X^-$ is chosen from organic and inorganic anions; and with the provisos that:
the group $B_1$ of formula (I) is linked to the radical A via any atom in the group A;
when k=0, the group A can be linked to the group $W_1$ directly via the nitrogen atom of the quaternary ammonium, in place of the radical $R_{10}$;
the group $B_2$ of formula (I) is linked to group A via any atom in the group A;
when m=0, the group A chosen from formula (VI) can be linked to the group $W_2$ directly via the nitrogen atom of the quaternary ammonium, in place of the radical $R_{10}$;
when k≠0, the group $B_1$ of formula (I) is linked to an atom of the group $W_1$, and said atom is chosen from atoms identified by an asterisk (*) on the skeleton of $W_1$ represented by formula (III) defined below; and
when m≠0, the group $B_2$ of formula (I) is linked to an atom of the group $W_2$ and said atom is chosen from atoms identified by an asterisk (*) on the skeleton of $W_2$ represented by formula (III) defined below;

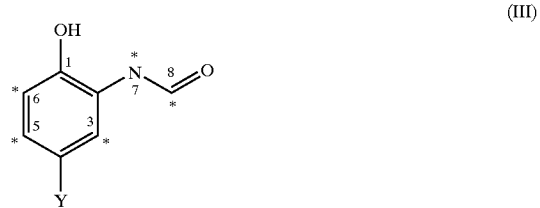

with the provisos that:
when k+l=0, at least one of $W_1$, $W_2$, and $B_2$ comprise at least one group Z;
when l+m=0, at least one of $W_1$, $W_2$, and $B_1$ comprise at least one group Z; and
when l=1, then k and m, independently, each have a value chosen from 0 and 1.

2. A composition according to claim 1, wherein the at least one coupler represents from 0.0005% to 12% by weight relative to the total weight of the composition.

3. A composition according to claim 1, wherein the at least one oxidation base is chosen from para-phenylenediamines, bis(phenyl)alkylenediamines, para-aminophenols, ortho-aminophenols and heterocyclic bases, and acid addition salts thereof.

4. A composition according to claim 1, wherein the at least one oxidation base represents from 0.0005% to 12% by weight relative to the total weight of the dye composition.

5. A composition according to claim 1, wherein, in addition to the at least one coupler, the composition further comprises at least one of (a) one or more additional couplers chosen from meta-phenylenediamines, meta-aminophenols, meta-diphenols and heterocyclic couplers, and acid addition salts thereof, and (b) one or more direct dyes.

6. A composition according to claim 5, wherein the one or more additional couplers represent from 0.0001% to 10% by weight relative to the total weight of the composition.

7. A composition according to claim 1, wherein the acid addition salts are chosen from the hydrochlorides, hydrobromides, sulphates, citrates, succinates, tartrates, lactates and acetates.

8. A process for the oxidation dyeing of keratin fibres comprising applying to the keratin fibres at least one dye composition comprising in a medium which is suitable for dyeing:

at least one oxidation base, and at least one coupler chosen from a cationic 2-acylaminophenol of formula (I) below or an acid addition salt thereof:

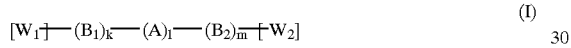

(I)

wherein:

A is a group chosen from a group D as defined below;

$B_1$ and $B_2$, independently, are each chosen from a group B as defined below;

k, l, and m, independently, are each integers having a value chosen from 0 and 1, wherein the sum k+l+m is not equal to zero;

$W_1$ and $W_2$, independently, are each chosen from a group W, wherein said group W is a group of formula (II) below:

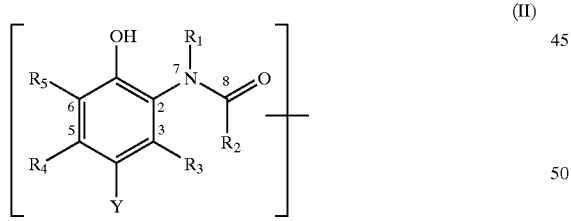

(II)

wherein:

$R_1$ is chosen from a hydrogen atom; a group Z as defined below; and linear and branched radicals comprising from 1 to 15 carbon atoms, wherein:

said branched radicals may form at least one carbon-based ring comprising from 3 to 7 ring members, said linear and branched radicals may comprise at least one double bond and/or at least one triple bond, wherein double bonds optionally lead to an aromatic group, at least one carbon atom of said linear and branched radicals, independently, may be replaced with a replacement chosen from oxygen, nitrogen, and sulphur atoms, and a $SO_2$ group, and said carbon atoms of said linear and branched radicals may, independently, be substituted with at least one halogen atom, with the provisos that the nitrogen atom in position 7 carrying $R_1$ is not linked directly to said $SO_2$ group; $R_1$ comprises no linkage chosen from peroxide linkages and no radicals chosen from diazo, nitro, and nitroso radicals; and $R_1$ is not chosen from hydroxyl, amino, thio, alkoxy, and alkylthio radicals;

$R_2$ is chosen from a hydrogen atom; a group Z as defined below; and linear and branched radicals comprising from 1 to 20 carbon atoms, wherein:

said branched radicals may form at least one carbon-based ring comprising from 3 to 7 ring members, said linear and branched radicals may comprise at least one double bond and/or at least one triple bond, wherein double bonds optionally lead to an aromatic group, at least one carbon atom of said linear and branched radicals, independently, may be replaced with a replacement chosen from oxygen, nitrogen, and sulphur atoms, and an $SO_2$ group, and said carbon atoms of said linear and branched radicals, independently, may be substituted with at least one halogen, with the provisos that $R_2$ comprises no linkage chosen from peroxide linkages and no radicals chosen from diazo, nitro, and nitroso radicals, and $R_2$ is not chosen from hydroxyl and thio groups;

$R_1$ and $R_2$ may be linked together to form a ring comprising from 5 to 7 ring members, wherein:

said ring is saturated or unsaturated, said ring members, independently, are each chosen from carbon, nitrogen, oxygen, and sulphur atoms, and a C=O group, said ring members, independently, are each unsubstituted or substituted with from 1 to 2 radicals chosen from R, R being chosen from linear and branched $C_1$–$C_6$ alkyl radicals, wherein:

said linear and branched $C_1$–$C_6$ alkyl radicals may form at least one ring comprising from 3 to 6 ring members, said linear and branched $C_1$–$C_6$ alkyl radicals may form at least one double and/or at least one triple bond, wherein double bonds optionally lead to an aromatic group, at least one carbon atom of said linear and branched $C_1$–$C_6$ alkyl radicals, independently, may be replaced with a replacement chosen from oxygen, nitrogen, and sulphur atoms, and an $SO_2$ group, the carbon atoms of said linear and branched $C_1$–$C_6$ alkyl radicals, independently, may be substituted with at least one halogen atom, and with the proviso that R comprises no linkage chosen from peroxide linkages and no radicals chosen from diazo, nitro, and nitroso radicals;

$R_3$, $R_4$, and $R_5$, which are identical or different, are each chosen from hydrogen and halogen atoms; a group Z as defined below; and linear and branched radicals comprising from 1 to 20 carbon atoms, wherein:

said linear and branched radicals may form at least one ring comprising from 3 to 7 ring members, said linear and branched radicals may comprise at least one double and/or at least one triple bond, wherein double bonds optionally lead to an aromatic group, at least one carbon atom of said linear and branched radicals, independently, may be replaced with a replacement chosen from oxygen, nitrogen, and sulphur atoms, and an SO$_2$ group, and the carbon atoms of said linear and branched radicals, independently, may be substituted with at least one halogen atom, with the provisos that R$_3$, R$_4$, and R$_5$ comprise no linkage chosen from peroxide linkages and no radicals chosen from diazo, nitro, and nitroso radicals; R$_5$ is not chosen from hydroxyl, thio, and amino groups, and substituted and unsubstituted sulphonylamino groups; and R$_3$, R$_4$, and R$_5$ are not linked to the benzene ring of formula (II) via an —NH—NH— linkage;

R$_1$ and R$_3$ are optionally linked together to form a saturated ring comprising from 6 to 7 ring members, wherein:
said ring members, independently, are each chosen from carbon, nitrogen, oxygen, and sulphur atoms, and a C=O group, and
said ring members, independently, are each unsubstituted or substituted with from 1 to 2 substituents, which may be the same or different, chosen from R, wherein R is defined above;

R$_2$ and R$_3$ are optionally linked together to form a saturated ring comprising from 5 to 7 ring members, wherein:
said ring members, independently, are each chosen from carbon, nitrogen, oxygen, and sulphur atoms, and a C=O group, and
said ring members, independently, are each unsubstituted or substituted with from 1 to 2 substituents, which may be identical or different, chosen from R, wherein R is defined above;

Y is chosen from hydrogen and halogen atoms; and —OR$_6$, —SR$_6$, and —NH—SO$_2$R$_6$ groups, wherein:
R$_6$ is chosen from linear and branched C$_1$–C$_6$ alkyl radicals,
said branched C$_1$–C$_6$ alkyl radicals may form at least one ring comprising from 3 to 6 ring members,
said linear and branched C$_1$–C$_6$ alkyl radicals are unsubstituted or substituted with at least one group chosen from a halogen atom; hydroxyl, C$_1$–C$_4$ alkoxy, amino, and C$_1$–C$_4$ aminoalkyl groups; a benzyl group; and a phenyl radical,
wherein said phenyl radical is unsubstituted or substituted with one or two substituents, which may be identical or different, chosen from C$_1$–C$_4$ alkyl, trifluoromethyl, carboxyl, (C$_1$–C$_4$)alkoxycarbonyl, halogen, hydroxyl, C$_1$–C$_4$ alkoxy, amino, and C$_1$–C$_4$ aminoalkyl groups; and
with the proviso that Y is not chosen from —NH—SO$_2$R$_6$ when R$_3$ is a hydroxyl group; and Z is a cationic group of formula (IV):

wherein:
B is chosen from linear and branched radicals comprising from 1 to 15 carbon atoms, wherein
said branched radicals may form at least one ring comprising from 3 to 7 ring members,
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an SO$_2$ group, and
the carbon atoms of said linear and branched radicals, independently, may be substituted with at least one substituent chosen from halogen atoms and a group Z; and
with the proviso that B comprises no linkage chosen from peroxide linkages and no radicals chosen from diazo, nitro, and nitroso radicals; and D is chosen from the cationic groups of formulae (V) and (VI):

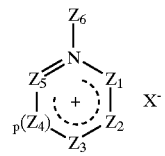

(V)

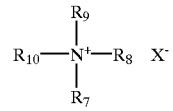

(VI)

wherein:
B is linked to the radical D by any atom in the radical D,
n and p, independently, each have a value chosen from 0 and 1,
when n=0, the group of formula (VI) can be linked to the compound of formula (II) directly via the nitrogen atom of the quaternary ammonium, in place of the radical R$_{10}$;
Z$_1$, Z$_2$, Z$_3$, and Z$_4$, independently, are each chosen from oxygen and sulphur atoms, nitrogen atoms which are unsubstituted or substituted with a substituent chosen from R$_{11}$, and carbon atoms which are unsubstituted or substituted with one or two substituents, which may be identical or different, chosen from R$_{11}$;
Z$_5$ is chosen from a nitrogen atom, and carbon atoms which are unsubstituted or substituted with a substituent chosen from R$_{11}$;
Z$_6$ is chosen from R$_{11}$, with the proviso that Z$_6$ is not a hydrogen atom;
Z$_6$ may form, with one of Z$_1$ and Z$_5$, a saturated or unsaturated ring comprising from 5 to 7 ring members, each ring member being unsubstituted or substituted with one or two substituents, which may be identical or different, chosen from R$_{11}$;
R$_{11}$ is chosen from a hydrogen atom; group Z; and linear and branched radicals comprising from 1 to 10 carbon atoms, wherein
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an SO$_2$ group, the carbon atoms of said linear and branched radicals, independently, may be substituted with at least one halogen, and with the proviso that said linear and branched radicals comprise no linkages chosen from peroxide linkages and no radicals chosen from diazo, nitro, and nitroso radicals;

adjacent pairs of radicals chosen from $Z_1$, $Z_2$, $Z_3$, $Z_4$, and $Z_5$ can optionally form a ring comprising from 5 to 7 ring members, wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms;

$R_7$, $R_8$, $R_9$, and $R_{10}$, which may be identical or different, are each chosen from $R_{11}$;

$R_7$, $R_8$, and $R_9$ may also form, in pairs with the quaternary nitrogen atom to which they are attached, at least one saturated ring comprising from 5 to 7 ring members, wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms; and $X^-$ is chosen from organic and inorganic anions; and with the provisos that:
the group $B_1$ of formula (I) is linked to the radical A via any atom in the group A;
when k=0, the group A can be linked to the group directly via the nitrogen atom of the quaternary ammonium, in place of the radical $R_{10}$;
the group $B_2$ of formula (I) is linked to group A via any atom in the group A;
when m=0, the group A chosen from formula (VI) can be linked to the group $W_2$ directly via the nitrogen atom of the quaternary ammonium, in place of the radical $R_{10}$;
when k≠0, the group $B_1$ of formula (I) is linked to an atom of the group $W_1$, and said atom is chosen from atoms identified by an asterisk (*) on the skeleton of $W_1$ represented by formula (III) defined below; and
when m≠0, the group $B_2$ of formula (I) is linked to an atom of the group $W_2$, and said atom is chosen from atoms identified by an asterisk (*) on the skeleton of $W_2$ represented by formula (III) defined below;

(III)

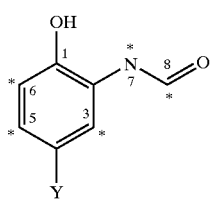

with the provisos that:
when k+l=0, at least one of $W_1$, $W_2$, and $B_2$ comprise at least one group Z;
when l+m=0, at least one of $W_1$, $W_2$, and $B_1$ comprise at least one group Z; and
when l=1, then k and m, independently, each have a value chosen from 0 and 1; and developing a color at acidic, neutral or alkaline pH using an oxidizing agent which is added to the dye composition just at the time of use, or which is present in an oxidizing composition applied simultaneously or sequentially in a separate manner.

9. A process according to claim 8, wherein the oxidizing agent is chosen from at least one of hydrogen peroxide, urea peroxide, alkali metal bromates, persalts and enzymes.

10. A multi-compartment device or multi-compartment dyeing "kit", comprising
a first compartment comprising a dye composition comprising in a medium which is suitable for dyeing:
at least one oxidation base, and
at least one coupler chosen from a cationic 2-acylaminophenol of formula (I) below or an acid addition salt thereof:

(I)

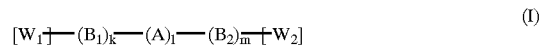

wherein:
A is a group chosen from a group D as defined below;
$B_1$ and $B_2$, independently, are each chosen from a group B as defined below;
k, l, and m, independently, are each integers having a value chosen from 0 and 1, wherein the sum k+l+m is not equal to zero;
$W_1$ and $W_2$, independently, are each chosen from a group W, wherein said group W is a group of formula (II) below:

(II)

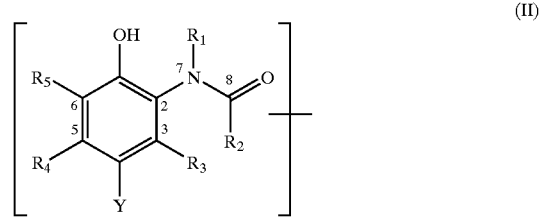

wherein:
$R_1$ is chosen from a hydrogen atom; a group Z as defined below; and linear and branched radicals comprising from 1 to 15 carbon atoms, wherein:
said branched radicals may form at least one carbon-based ring comprising from 3 to 7 ring members,
said linear and branched radicals may comprise at least one double bond and/or at least one triple bond, wherein double bonds optionally lead to an aromatic group,
at least one carbon atom of said linear and branched radicals, independently, may be replaced with a replacement chosen from oxygen, nitrogen, and sulphur atoms, and a $SO_2$ group, and
said carbon atoms of said linear and branched radicals may, independently, be substituted with at least one halogen atom,
with the provisos that the nitrogen atom in position 7 carrying $R_1$ is not linked directly to said $SO_2$ group; $R_1$ comprises no linkage chosen from peroxide linkages and no radicals chosen from diazo, nitro, and nitroso radicals; and $R_1$ is not chosen from hydroxyl, amino, thio, alkoxy, and alkylthio radicals;

$R_2$ is chosen from a hydrogen atom; a group Z as defined below; and linear and branched radicals comprising from 1 to 20 carbon atoms, wherein:
  said branched radicals may form at least one carbon-based ring comprising from 3 to 7 ring members,
  said linear and branched radicals may comprise at least one double bond and/or at least one triple bond, wherein double bonds optionally lead to an aromatic group,
  at least one carbon atom of said linear and branched radicals, independently, may be replaced with a replacement chosen from oxygen, nitrogen, and sulphur atoms, and an $SO_2$ group, and
  said carbon atoms of said linear and branched radicals, independently, may be substituted with at least one halogen,
  with the provisos that $R_2$ comprises no linkage chosen from peroxide linkages and no radicals chosen from diazo, nitro, and nitroso radicals, and $R_2$ is not chosen from hydroxyl and thio groups;

$R_1$ and $R_2$ may be linked together to form a ring comprising from 5 to 7 ring members, wherein:
  said ring is saturated or unsaturated,
  said ring members, independently, are each chosen from carbon, nitrogen, oxygen, and sulphur atoms, and a C=O group,
  said ring members, independently, are each unsubstituted or substituted with from 1 to 2 radicals chosen from R, R being chosen from linear and branched $C_1$–$C_6$ alkyl radicals, wherein:
    said linear and branched $C_1$–$C_6$ alkyl radicals may form at least one ring comprising from 3 to 6 ring members,
    said linear and branched $C_1$–$C_6$ alkyl radicals may form at least one double and/or at least one triple bond, wherein double bonds optionally lead to an aromatic group,
    at least one carbon atom of said linear and branched $C_1$–$C_6$ alkyl radicals, independently, may be replaced with a replacement chosen from oxygen, nitrogen, and sulphur atoms, and an $SO_2$ group,
    the carbon atoms of said linear and branched $C_1$–$C_6$ alkyl radicals, independently, may be substituted with at least one halogen atom, and
    with the proviso that R comprises no linkage chosen from peroxide linkages and no radicals chosen from diazo, nitro, and nitroso radicals;

$R_3$, $R_4$, and $R_5$, which are identical or different, are each chosen from hydrogen and halogen atoms; a group Z as defined below; and linear and branched radicals comprising from 1 to 20 carbon atoms, wherein:
  said linear and branched radicals may form at least one ring comprising from 3 to 7 ring members,
  said linear and branched radicals may comprise at least one double and/or at least one triple bond, wherein double bonds optionally lead to an aromatic group,
  at least one carbon atom of said linear and branched radicals, independently, may be replaced with a replacement chosen from oxygen, nitrogen, and sulphur atoms, and an $SO_2$ group, and
  the carbon atoms of said linear and branched radicals, independently, may be substituted with at least one halogen atom,
  with the provisos that $R_3$, $R_4$, and $R_5$ comprise no linkage chosen from peroxide linkages and no radicals chosen from diazo, nitro, and nitroso radicals; $R_5$ is not chosen from hydroxyl, thio, and amino groups, and substituted and unsubstituted sulphonylamino groups; and $R_3$, $R_4$, and $R_5$ are not linked to the benzene ring of formula (II) via an —NH—NH— linkage;

$R_1$ and $R_3$ are optionally linked together to form a saturated ring comprising from 6 to 7 ring members, wherein:
  said ring members, independently, are each chosen from carbon, nitrogen, oxygen, and sulphur atoms, and a C=O group, and
  said ring members, independently, are each unsubstituted or substituted with from 1 to 2 substituents, which may be the same or different, chosen from R, wherein R is defined above;

$R_2$ and $R_3$ are optionally linked together to form a saturated ring comprising from 5 to 7 ring members, wherein:
  said ring members, independently, are each chosen from carbon, nitrogen, oxygen, and sulphur atoms, and a C=O group, and
  said ring members, independently, are each unsubstituted or substituted with from 1 to 2 substituents, which may be identical or different, chosen from R, wherein R is defined above;

Y is chosen from hydrogen and halogen atoms; and —$OR_6$, —$SR_6$, and —NH—$SO_2R_6$ groups, wherein:
  $R_6$ is chosen from linear and branched $C_1$–$C_6$ alkyl radicals,
  said branched $C_1$–$C_6$ alkyl radicals may form at least one ring comprising from 3 to 6 ring members,
  said linear and branched $C_1$–$C_6$ alkyl radicals are unsubstituted or substituted with at least one group chosen from a halogen atom; hydroxyl, $C_1$–$C_4$ alkoxy, amino, and $C_1$–$C_4$ aminoalkyl groups; a benzyl group; and a phenyl radical, wherein said phenyl radical is unsubstituted or substituted with one or two substituents, which may be identical or different, chosen from $C_1$–$C_4$ alkyl, trifluoromethyl, carboxyl, ($C_1$–$C_4$)alkoxycarbonyl, halogen, hydroxyl, $C_1$–$C_4$ alkoxy, amino, and $C_1$–$C_4$ aminoalkyl groups; and
  with the proviso that Y is not chosen from —NH—$SO_2R_6$ when $R_3$ is a hydroxyl group; and Z is a cationic group of formula (IV):

$$-(B)_n-D \qquad (IV)$$

wherein:
B is chosen from linear and branched radicals comprising from 1 to 15 carbon atoms, wherein
said branched radicals may form at least one ring comprising from 3 to 7 ring members,
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group, and
the carbon atoms of said linear and branched radicals, independently, may be substituted with at least one substituent chosen from halogen atoms and a group Z; and
with the proviso that B comprises no linkage chosen from peroxide linkages and no radicals chosen from diazo, nitro, and nitroso radicals; and
D is chosen from the cationic groups of formulae (V) and (VI):

(V)

(VI)

wherein:
B is linked to the radical D by any atom in the radical D,
n and p, independently, each have a value chosen from 0 and 1,
when n=0, the group of formula (VI) can be linked to the compound of formula (II) directly via the nitrogen atom of the quaternary ammonium, in place of the radical $R_{10}$,
$Z_1$, $Z_2$, $Z_3$, and $Z_4$, independently, are each chosen from oxygen and sulphur atoms, nitrogen atoms which are unsubstituted or substituted with a substituent chosen from $R_{11}$, and carbon atoms which are unsubstituted or substituted with one or two substituents, which may be identical or different, chosen from $R_{11}$;
$Z_5$ is chosen from a nitrogen atom, and carbon atoms which are unsubstituted or substituted with a substituent chosen from $R_{11}$;
$Z_6$ is chosen from $R_{11}$, with the proviso that $Z_6$ is not a hydrogen atom;
$Z_6$ may form, with one of $Z_1$ and $Z_5$, a saturated or unsaturated ring comprising from 5 to 7 ring members, each ring member being unsubstituted or substituted with one or two substituents, which may be identical or different, chosen from $R_{11}$;
$R_{11}$ is chosen from a hydrogen atom; group Z; and linear and branched radicals comprising from 1 to 10 carbon atoms, wherein
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group,
the carbon atoms of said linear and branched radicals, independently, may be substituted with at least one halogen, and
with the proviso that said linear and branched radicals comprise no linkages chosen from peroxide linkages and no radicals chosen from diazo, nitro, and nitroso radicals;
adjacent pairs of radicals chosen from $Z_1$, $Z_2$, $Z_3$, $Z_4$, and $Z_5$ can optionally form a ring comprising from 5 to 7 ring members,
wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms;
$R_7$, $R_8$, $R_9$, and $R_{10}$, which may be identical or different, are each chosen from $R_{11}$;
$R_7$, $R_8$, and $R_9$ may also form, in pairs with the quaternary nitrogen atom to which they are attached, at least one saturated ring comprising from 5 to 7 ring members,
wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms; and
$X^-$ is chosen from organic and inorganic anions; and
with the provisos that:
the group $B_1$ of formula (I) is linked to the radical A via any atom in the group A;
when k=0, the group A can be linked to the group $W_1$ directly via the nitrogen atom of the quaternary ammonium, in place of the radical $R_{10}$;
the group $B_2$ of formula (I) is linked to group A via any atom in the group A;
when m=0, the group A chosen from formula (VI) can be linked to the group $W_2$ directly via the nitrogen atom of the quaternary ammonium, in place of the radical $R_{10}$;
when k≠0, the group $B_1$ of formula (I) is linked to an atom of the group $W_1$, and said atom is chosen from atoms identified by an asterisk (*) on the skeleton of $W_1$ represented by formula (III) defined below; and
when m≠0, the group $B_2$ of formula (I) is linked to an atom of the group $W_2$ and said atom is chosen from atoms identified by an asterisk (*) on the skeleton of $W_2$ represented by formula (III) defined below;

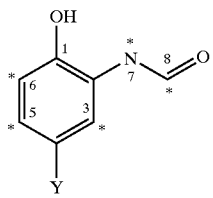

(III)

with the provisos that:
when k+l=0, at least one of $W_1$, $W_2$, and $B_2$ comprise at least one group Z;
when l+m=0, at least one of $W_1$, $W_2$, and $B_1$ comprise at least one group Z; and
when l=1, then k and m, independently, each have a value chosen from 0 and 1; and
a second compartment comprising an oxidizing composition.

11. A cationic 2-acylaminophenol of formula (I) below or an acid addition salt thereof:

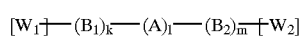

(I)

wherein:
A is a group chosen from a group D as defined below;
$B_1$ and $B_2$, independently, are each chosen from a group B as defined below;
k, l, and m, independently, are each integers having a value chosen from 0 and 1, wherein the sum k+l+m is not equal to zero;
$W_1$ and $W_2$, independently, are each chosen from a group W, wherein said group W is a group of formula (II) below:

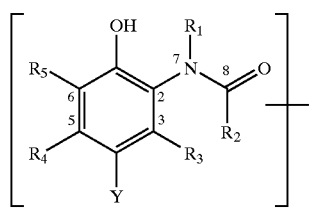

(II)

wherein:
$R_1$ is chosen from a hydrogen atom; a group Z as defined below; and linear and branched radicals comprising from 1 to 15 carbon atoms, wherein:
said branched radicals may form at least one carbon-based ring comprising from 3 to 7 ring members,
said linear and branched radicals may comprise at least one double bond and/or at least one triple bond, wherein double bonds optionally lead to an aromatic group,
at least one carbon atom of said linear and branched radicals, independently, may be replaced with a replacement chosen from oxygen, nitrogen, and sulphur atoms, and a $SO_2$ group, and
said carbon atoms of said linear and branched radicals may, independently, be substituted with at least one halogen atom, with the provisos that the nitrogen atom in position 7 carrying $R_1$ is not linked directly to said $SO_2$ group; $R_1$ comprises no linkage chosen from peroxide linkages and no radicals chosen from diazo, nitro, and nitroso radicals; and $R_1$ is not chosen from hydroxyl, amino, thio, alkoxy, and alkylthio radicals;

$R_2$ is chosen from a hydrogen atom; a group Z as defined below; and linear and branched radicals comprising from 1 to 20 carbon atoms, wherein:
said branched radicals may form at least one carbon-based ring comprising from 3 to 7 ring members,
said linear and branched radicals may comprise at least one double bond and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group, and
said carbon atoms of said linear and branched radicals, independently, may be substituted with at least one halogen, with the provisos that $R_2$ comprises no linkage chosen from peroxide linkages and no radicals chosen from diazo, nitro, and nitroso radicals, and $R_2$ is not chosen from hydroxyl and thio groups;
$R_1$ and $R_2$ may be linked together to form a ring comprising from 5 to 7 ring members, wherein:
said ring is saturated or unsaturated,
said ring members, independently, are each chosen from carbon, nitrogen, oxygen, and sulphur atoms, and a C=O group,
said ring members, independently, are each unsubstituted or substituted with from 1 to 2 radicals chosen from R, R being chosen from linear and branched $C_1$–$C_6$ alkyl radicals, wherein:
said linear and branched $C_1$–$C_6$ alkyl radicals may form at least one ring comprising from 3 to 6 ring members,
said linear and branched $C_1$–$C_6$ alkyl radicals may form at least one double and/or at least one triple bond, wherein double bonds optionally lead to an aromatic group,
at least one carbon atom of said linear and branched $C_1$–$C_6$ alkyl radicals, independently, may be replaced with a replacement chosen from oxygen, nitrogen, and sulphur atoms, and an $SO_2$ group,
the carbon atoms of said linear and branched $C_1$–$C_6$ alkyl radicals, independently, may be substituted with at least one halogen atom, and
with the proviso that R comprises no linkage chosen from peroxide linkages and no radicals chosen from diazo, nitro, and nitroso radicals;
$R_3$, $R_4$, and $R_5$, which are identical or different, are each chosen from hydrogen and halogen atoms; a group Z as defined below; and linear and branched radicals comprising from 1 to 20 carbon atoms, wherein:
said linear and branched radicals may form at least one ring comprising from 3 to 7 ring members,
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group, and
the carbon atoms of said linear and branched radicals, independently, may be substituted with at least one halogen atom,
with the provisos that $R_3$, $R_4$, and $R_5$ comprise no linkage chosen from peroxide linkages and no radicals chosen from diazo, nitro, and nitroso radicals; $R_5$ is not chosen from hydroxyl, thio, and amino groups, and substituted and unsubstituted sulphonylamino groups; and $R_3$, $R_4$, and $R_5$ are not linked to the benzene ring of formula (II) via an —NH—NH— linkage;

$R_1$ and $R_3$ are optionally linked together to form a saturated ring comprising from 6 to 7 ring members, wherein:
said ring members, independently, are each chosen from carbon, nitrogen, oxygen, and sulphur atoms, and a C=O group, and
said ring members, independently, are each unsubstituted or substituted with from 1 to 2 substituents, which may be the same or different, chosen from R, wherein R is defined above;

$R_2$ and $R_3$ are optionally linked together to form a saturated ring comprising from 5 to 7 ring members, wherein:
said ring members, independently, are each chosen from carbon, nitrogen, oxygen, and sulphur atoms, and a C=O group, and
said ring members, independently, are each unsubstituted or substituted with from 1 to 2 substituents, which may be identical or different, chosen from R, wherein R is defined above;

Y is chosen from hydrogen and halogen atoms; and —$OR_6$, —$SR_6$, and —NH—$SO_2R_6$ groups, wherein:
$R_6$ is chosen from linear and branched $C_1$–$C_6$ alkyl radicals,
said branched $C_1$–$C_6$ alkyl radicals may form at least one ring comprising from 3 to 6 ring members,
said linear and branched $C_1$–$C_6$ alkyl radicals are unsubstituted or substituted with at least one group chosen from a halogen atom; hydroxyl, $C_1$–$C_4$ alkoxy, amino, and $C_1$–$C_4$ aminoalkyl groups; a benzyl group; and a phenyl radical,
wherein said phenyl radical is unsubstituted or substituted with one or two substituents, which may be identical or different, chosen from $C_1$–$C_4$ alkyl, trifluoromethyl, carboxyl, ($C_1$–$C_4$) alkoxycarbonyl, halogen, hydroxyl, $C_1$–$C_4$ alkoxy, amino, and $C_1$–$C_4$ aminoalkyl groups; and
with the proviso that Y is not chosen from —NH—$SO_2R_6$ when $R_3$ is a hydroxyl group; and Z is a cationic group of formula (IV):

wherein:
B is chosen from linear and branched radicals comprising from 1 to 15 carbon atoms, wherein
said branched radicals may form at least one ring comprising from 3 to 7 ring members,
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group, and
the carbon atoms of said linear and branched radicals, independently, may be substituted with at least one substituent chosen from halogen atoms and a group Z; and
with the proviso that B comprises no linkage chosen from peroxide linkages and no radicals chosen from diazo, nitro, and nitroso radicals; and
D is chosen from the cationic groups of formulae (V) and (VI):

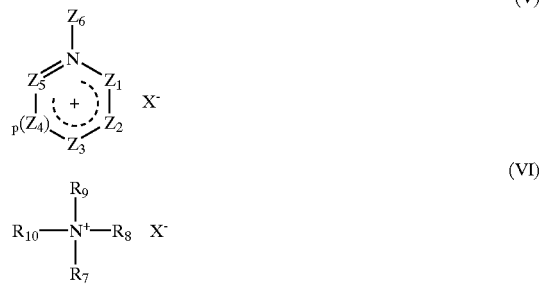

wherein:
B is linked to the radical D by any atom in the radical D,
n and p, independently, each have a value chosen from 0 and 1,
when n=0, the group of formula (VI) can be linked to the compound of formula (II) directly via the nitrogen atom of the quaternary ammonium, in place of the radical $R_{10}$;
$Z_1$, $Z_2$, $Z_3$, and $Z_4$, independently, are each chosen from oxygen and sulphur atoms, nitrogen atoms which are unsubstituted or substituted with a substituent chosen from $R_{11}$, and carbon atoms which are unsubstituted or substituted with one or two substituents, which may be identical or different, chosen from $R_{11}$;
$Z_5$ is chosen from a nitrogen atom, and carbon atoms which are unsubstituted or substituted with a substituent chosen from $R_{11}$;
$Z_6$ is chosen from $R_{11}$, with the proviso that $Z_6$ is not a hydrogen atom;
$Z_6$ may form, with one of $Z_1$ and $Z_5$, a saturated or unsaturated ring comprising from 5 to 7 ring members, each ring member being unsubstituted or substituted with one or two substituents, which may be identical or different, chosen from $R_{11}$;
$R_{11}$ is chosen from a hydrogen atom; group Z; and linear and branched radicals comprising from 1 to 10 carbon atoms, wherein
said linear and branched radicals may comprise at least one double and/or at least one triple bond, wherein double bonds optionally lead to an aromatic group,
at least one carbon atom of said linear and branched radicals, independently, may be replaced with a replacement chosen from oxygen, nitrogen, and sulphur atoms, and an $SO_2$ group,
the carbon atoms of said linear and branched radicals, independently, may be substituted with at least one halogen, and
with the proviso that said linear and branched radicals comprise no linkages chosen from peroxide linkages and no radicals chosen from diazo, nitro, and nitroso radicals;

adjacent pairs of radicals chosen from $Z_1$, $Z_2$, $Z_3$, $Z_4$, and $Z_5$ can optionally form a ring comprising from 5 to 7 ring members,
wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms;

$R_7$, $R_8$, $R_9$, and $R_{10}$, which may be identical or different, are each chosen from $R_{11}$;

$R_7$, $R_8$, and $R_9$ may also form, in pairs with the quaternary nitrogen atom to which they are attached, at least one saturated ring comprising from 5 to 7 ring members, wherein said ring members, independently, are each chosen from carbon atoms which are unsubstituted or substituted with one or two substituents, which may be identical or different, chosen from $R_{11}$; nitrogen atoms which are unsubstituted or substituted with a substituent chosen from $R_{11}$; and oxygen and sulphur atoms; and $X^-$ is chosen from organic and inorganic anions; and with the provisos that:

the group $B_1$ of formula (I) is linked to the radical A via any atom in the group A;

when k=0, the group A can be linked to the group $W_1$ directly via the nitrogen atom of the quaternary ammonium, in place of the radical $R_{10}$;

the group B2 of formula (I) is linked to group A via any atom in the group A;

when m=0, the group A chosen from formula (VI) can be linked to the group $W_2$ directly via the nitrogen atom of the quaternary ammonium, in place of the radical $R_{10}$;

when k≠0, the group $B_1$ of formula (I) is linked to an atom of the group $W_1$, and said atom is chosen from atoms identified by an asterisk (*) on the skeleton of $W_1$ represented by formula (III) defined below; and when m≠0, the group $B_2$ of formula (I) is linked to an atom of the group $W_2$ and said atom is chosen from atoms identified by an asterisk (*) on the skeleton of $W_2$ represented by formula (III) defined below;

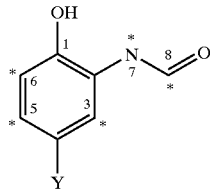

(III)

with the provisos that:
when k+l=0, at least one of $W_1$, $W_2$, and $B_2$ comprise at least one group Z;
when l+m=0, at least one of $W_1$, $W_2$, and $B_1$ comprise at least one group Z; and
when l=1, then k and m, independently, each have a value chosen from 0 and 1.

12. The cationic 2-acylaminophenol of claim 11, wherein $R_1$ in formula (II) is chosen from a hydrogen atom, a group Z, a group $A_1$, a group $A_2$, a group $A_3$, a group $A_4$, and a group $A_5$, wherein:

the groups $A_1$, $A_2$, $A_3$, $A_4$, and $A_5$ may be separated from the nitrogen located in position 7, to which the radical $R_1$ is attached, by a —(CO)— group;

$A_1$ is chosen from linear and branched $C_1$–$C_8$ alkyl radicals,
wherein said linear and branched $C_1$–$C_8$ alkyl radicals may comprise one double bond, two double bonds, or one triple bond,
said linear and branched $C_1$–$C_8$ alkyl radicals may be unsubstituted or substituted with at least one substituent chosen from group $A_2$, group $A_4$, and group $A_5$; said linear and branched $C_1$–$C_8$ alkyl radicals may be substituted with one or two groups, which may be identical or different, chosen from N—($C_1$-$C_3$)alkylamino, N—($C_1$-$C_3$)alkyl-N—($C_1$-$C_3$)alkylamino, ($C_1$-$C_6$)alkoxy, oxo, alkoxycarbonyl, acyloxy, amide, acylamino, ureyl, sulphoxy, sulphonyl, sulphonamido, sulphonylamino, bromo, cyano, and carboxyl groups; and said linear and branched $C_1$–$C_8$ alkyl radicals may be substituted with at least one substituent chosen from hydroxyl, fluoro, and chloro groups, $A_2$ is chosen from aromatic groups, wherein said aromatic groups may be unsubstituted or substituted with one to three groups, which may be identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano groups, $A_3$ is chosen from heteroaromatic groups chosen from furyl, thienyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolyl, benzimidazolyl, and benzopyrimidyl groups, wherein
said heteroaromatic groups are unsubstituted or substituted with from 1 to 3 substituents, which may be identical or different, chosen from linear and branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino, and hydroxyl groups, $A_4$ is chosen from $C_3$–$C_7$ cycloalkyl groups, and norbornanyl radicals, wherein said norbornanyl radicals may comprise a double bond, and may be unsubstituted or substituted with from 1 to 2 substituents, which may be the same or different, chosen from linear and branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino, and hydroxyl radicals, and $A_5$ is chosen from heterocycles chosen from dihydrofuryl, tetrahydrofuryl, butyrolactonyl, dihydrothienyl, tetrahydrothienyl, tetrahydrothienonyl, iminothiolane, dihydropyrrolyl, pyrrolidinyl, pyrrolidinonyl, imidazolidinonyl, imidazolidinothienyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridyl, piperidyl, pentalactam, morpholinyl, pyrazoli(di)nyl, pyrimi(di)nyl, pyrazinyl, piperazinyl, and azepinyl rings.

13. The cationic 2-acylaminophenol of claim 12, wherein $A_2$ is chosen from phenyl and naphthyl groups, which may be unsubstituted or substituted as defined in claim 12.

14. The cationic 2-acylaminophenol of claim 11, wherein $R_1$ in formula (II) is chosen from a hydrogen atom; methyl, ethyl, isopropyl, allyl, phenyl, benzyl, fluorobenzyl, hydroxybenzyl, difluorobenzyl, trifluorobenzyl, chlorobenzyl, bromobenzyl, methoxybenzyl, dimethoxybenzyl, (trifluoromethoxy)benzyl, 3,4-methylenedioxybenzyl, 6-chloropiperonyl, 4-methylthiobenzyl, 4-methylsulphonylbenzyl, 4-acetylaminobenzyl, 4-carboxybenzyl, 1-naphthomethyl, 2-naphthomethyl, and 2-hydroxyethyl, 2-methoxyethyl, and 2-ethoxyethyl groups.

15. The cationic 2-acylaminophenol of claim 11, wherein $R_2$ in formula (II) is chosen from a hydrogen atom; an amino group; a group Z; and $A_1$, $A_2$, $A_3$, $A_4$, and $A_5$ groups, wherein:

the groups $A_1$, $A_2$, $A_3$, $A_4$, and $A_5$ are optionally separated from the carbon located in position 8 of the amide function of the compound of formula (II) by a groups chosen from —O—, —NH, and —N—$(C_1-C_3)$alkyl groups;

$A_1$ is chosen from linear and branched $C_1-C_8$ alkyl radicals,
wherein said linear and branched $C_1-C_8$ alkyl radicals may comprise one double bond, two double bonds, or one triple bond,
said linear and branched $C_1-C_8$ alkyl radicals may be unsubstituted or substituted with at least one substituent chosen from group $A_2$, group $A_4$, and group $A_5$; said linear and branched $C_1-C_8$ alkyl radicals may be substituted with one or two groups, which may be identical or different, chosen from N—$(C_1-C_3)$alkylamino, N—$(C_1-C_3)$alkyl-N—$(C_1-C_3)$alkylamino, $(C_1-C_6)$alkoxy, oxo, alkoxycarbonyl, acyloxy, amide, acylamino, ureyl, sulphoxy, sulphonyl, sulphonamido, sulphonylamino, bromo, cyano, and carboxyl groups; and said linear and branched $C_1-C_8$ alkyl radicals may be substituted with at least one substituent chosen from hydroxyl, fluoro, and chloro groups, $A_2$ is chosen from aromatic groups, wherein said aromatic groups may be unsubstituted or substituted with one to three groups, which may be identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano groups, $A_3$ is chosen from heteroaromatic groups chosen from furyl, thienyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolyl, benzimidazolyl, and benzopyrimidyl groups, wherein
said heteroaromatic groups are unsubstituted or substituted with from 1 to 3 substituents, which may be identical or different, chosen from linear and branched $C_1-C_4$ alkyl, $C_1-C_4$ monohydroxyalkyl, $C_2-C_4$ polyhydroxyalkyl, carboxyl, alkoxycarbonyl, halogen, amido, amino, and hydroxyl groups, $A_4$ is chosen from $C_3-C_7$ cycloalkyl groups, and norbornanyl radicals, wherein said norbornanyl radicals may comprise a double bond, and may be unsubstituted or substituted with from 1 to 2 substituents, which may be the same or different, chosen from linear and branched $C_1-C_4$ alkyl, $C_1-C_4$ monohydroxyalkyl, $C_2-C_4$ polyhydroxyalkyl, carboxyl, alkoxycarbonyl, halogen, amido, amino, and hydroxyl radicals, and $A_5$ is chosen from heterocycles chosen from dihydrofuryl, tetrahydrofuryl, butyrolactonyl, dihydrothienyl, tetrahydrothienyl, tetrahydrothienonyl, iminothiolane, dihydropyrrolyl, pyrrolidinyl, pyrrolidinonyl, imidazolidinonyl, imidazolidinothienyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridyl, piperidyl, pentalactam, morpholinyl, pyrazoli(di)nyl, pyrimi(di)nyl, pyrazinyl, piperazinyl, and azepinyl rings.

16. The cationic 2-acylaminophenol of claim 11, wherein $R_2$ of formula (II) is chosen from a group Z; and a group (G1), wherein
said group (G1) is chosen from methyl, ethyl, propyl, isopropyl, butyl, isobutyl, tert-butyl, pentyl, isopentyl, neopentyl, hexyl, cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl, tetrahydrofur-2-yl, fur-2-yl, 5-methyl-2-(trifluoromethyl)fur-3-yl, 2-methyl-5-phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tertbutyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy, amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl, and 4-morpholinyl groups.

17. The cationic 2-acylaminophenol of claim 11, wherein, in formula (II), $R_1$ and $R_2$ together form a ring, said ring being chosen from 2-pyrrolidinon-1-yl, methyl-2-pyrrolidinon-1-yl, 5-carboxy-2-pyrrolidinon-1-yl, 5-methoxycarbonyl-2-pyrrolidinon-1-yl, pyrazolinon-1-yl, succinimid-1-yl, 3,5-diketopyrazolidin-1-yl, oxindolin-1-yl, maleimid-1-yl, isoindole-1,3-dion-2-yl, 2-piperidinon-1-yl, and glutarimid-1-yl groups.

18. The cationic 2-acylaminophenol of claim 11, wherein $R_2$ of formula (11) is chosen from group (G2), and —$D_1$, —E—$D_1$, —O—E—$D_1$, and —NH—E—$D_1$ groups, wherein:
    said group (G2) is chosen from methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl, and 4-morpholinyl groups;
    —E— is chosen from —(CH$_2$)$_q$— groups, q being an integer having a value chosen from 1 and 2; and
    $D_1$ is chosen from a group D', wherein group D' is chosen from 3-methylimidazolidinium-1-yl, 3-(2-hydroxyethyl)imidazolidinium-1-yl, 1,2,4-triazolinium-1-yl, 1,2,4-triazolinium-4-yl, N—($C_1$–$C_4$) alkylpyridinium-2-yl, N—($C_1$–$C_4$)alkylpyridinium-3-yl, N—($C_1$–$C_4$)alkylpyridinium-4-yl, N-(2-hydroxyethyl)pyridinium-2-yl, N-(2-hydroxyethyl) pyridinium-3-yl, N-(2-hydroxyethyl)pyridinium-4-yl, pyridinium-1-yl, tri($C_1$–$C_4$)alkylammonium-N-yl, 1-methylpiperidinium-1-yl, and 1,4-dimethylpiperazinium-1-yl groups.

19. The cationic 2-acylaminophenol of claim 18, wherein $R_2$ of formula (II) is chosen from methyl, methoxymethyl, 2-carboxyethyl, methoxy, amino, ethylamino, and 1-pyrrolidinyl groups; and —$D_1$, —E—$D_1$, —O—E—$D_1$, and —NH—E—$D_1$ groups.

20. The cationic 2-acylaminophenol of claim 11, wherein, in formula (II), $R_3$ and $R_4$, which may be identical or different, are each chosen from hydrogen and halogen atoms; hydroxyl and amino groups; a group Z; and $A_1$, $A_2$, $A_3$, $A_4$, and $A_5$ groups optionally separated from the phenolic nucleus of formula (II) by at least one group chosen from an oxygen atom and —NH—, —N($C_1$–$C_3$)alkyl-, —NH(CO)—, —N($C_1$–$C_3$)alkyl-CO—, —NH[C=NH]—, —NH(CO)NH—, —NH(CO)N($C_1$–$C_3$)alkyl-, —NH(CO)O—, —NHSO$_2$—, —NHSO$_2$NH—, and —NHSO$_2$N($C_1$–$C_3$)alkyl- groups, wherein:
    $A_1$ is chosen from linear and branched $C_1$–$C_8$ alkyl radicals,
        wherein said linear and branched $C_1$–$C_8$ alkyl radicals may comprise one double bond, two double bonds, or one triple bond,
        said linear and branched $C_1$–$C_8$ alkyl radicals may be unsubstituted or substituted with at least one substituent chosen from group $A_2$, group $A_4$, and group $A_5$; said linear and branched $C_1$–$C_8$ alkyl radicals may be substituted with one or two groups, which may be identical or different, chosen from N—($C_1$–$C_3$)alkylamino, N—($C_1$–$C_3$)alkyl-N—($C_1$–$C_3$)alkylamino, ($C_1$–$C_6$)alkoxy, oxo, alkoxycarbonyl, acyloxy, amide, acylamino, ureyl, sulphoxy, sulphonyl, sulphonamido, sulphonylamino, bromo, cyano, and carboxyl groups; and said linear and branched $C_1$–$C_8$ alkyl radicals may be substituted with at least one substituent chosen from hydroxyl, fluoro, and chloro groups,
    $A_2$ is chosen from aromatic groups, wherein said aromatic groups may be unsubstituted or substituted with one to three groups, which may be identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano groups,
    $A_3$ is chosen from heteroaromatic groups chosen from furyl, thienyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolyl, benzimidazolyl, and benzopyrimidyl groups, wherein
        said heteroaromatic groups are unsubstituted or substituted with from 1 to 3 substituents, which may be identical or different, chosen from linear and branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino, and hydroxyl groups,
    $A_4$ is chosen from $C_3$–$C_7$ cycloalkyl groups, and norbornanyl radicals, wherein said norbornanyl radicals may comprise a double bond, and may be unsubstituted or substituted with from 1 to 2 substituents, which may be the same or different, chosen from linear and branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino, and hydroxyl radicals, and
    $A_5$ is chosen from heterocycles chosen from dihydrofuryl, tetrahydrofuryl, butyrolactonyl, dihydrothienyl, tetrahydrothienyl, tetrahydrothienonyl, iminothiolane, dihydropyrrolyl, pyrrolidinyl, pyrrolidinonyl, imidazolidinonyl, imidazolidinothienyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridyl, piperidyl, pentalactam, morpholinyl, pyrazoli(di)nyl, pyrimi(di)nyl, pyrazinyl, piperazinyl, and azepinyl rings.

21. The cationic 2-acylaminophenol of claim 20, wherein $R_3$ of formula (II) is chosen from hydrogen and chlorine atoms; a group Z; methyl, hydroxymethyl, methoxymethyl, 1-hydroxyethyl, aminomethyl, methylaminomethyl, hydroxyl, methoxy, amino, methylamino, and 2-hydroxyethylamino groups; a group —NH(CO)$R_{12}$ wherein $R_{12}$ is chosen from a group (G1); and a group —NHSO$_2$R$_{13}$ groups, wherein $R_{13}$ is chosen from a group (G3), wherein
    said group (G1) is chosen from methyl, ethyl, propyl, isopropyl, butyl, isobutyl, tert-butyl, pentyl, isopentyl, neopentyl, hexyl, cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl) phenyl, hydroxyphenyl, methoxyphenyl, ethoxyphenyl, acetoxyphenyl, (trifluoromethoxy) phenyl, aminophenyl, 4-dimethylaminophenyl, fluorophenyl, difluorophenyl, fluoro(trifluoromethyl) phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl, tetrahydrofur-2-yl, fur-2-yl, 5-methyl-2-(trifluoromethyl)fur-3-yl, 2-methyl-5-phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tertbutyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl) methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy, amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl) phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl, and 4-morpholinyl groups; and said group (G3) is chosen from methyl, trifluoromethyl, ethyl, 2-chloroethyl, propyl, 3-chloropropyl, isopropyl, butyl, thien-2-yl, hydroxyl, ethoxy, and dimethylamino groups.

22. The cationic 2-acylaminophenol of claim 21, wherein $R_3$ in formula (II) is chosen from a hydrogen atom; methyl, hydroxymethyl, aminomethyl, hydroxyl, methoxy, amino, and methylamino groups; a methanesulphonylamino group; an ethanesulphonylamino group; a dimethylaminosulphonylamino group; —NH(CO)$R_{14}$ groups, wherein $R_{14}$ is chosen from group (G2); and —O—E—$D_2$, —NH—E—$D_2$, —NH (CO)—$D_2$, —NH(CO)—E—$D_2$, —NH(CO)O—E—$D_2$, —NH(CO)NH—E—$D_2$, and —NH(SO$_2$)—E—$D_2$ groups, wherein:

said group (G2) is chosen from methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl, and 4-morpholinyl groups;

—E— is chosen from —(CH$_2$)$_q$— groups, q being an integer having a value chosen from 1 and 2; and $D_2$ is chosen from a group D', wherein group D' is chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C$_1$–C$_4$) alkylpyridinium-2-yl, N—(C$_1$–C$_4$)alkylpyridinium-3-yl, N—(C$_1$–C$_4$)alkylpyridinium-4-yl, N-(2-hydroxyethyl)pyridinium-2-yl, N-(2-hydroxyethyl) pyridinium-3-yl, N-(2-hydroxyethyl)pyridinium-4-yl, pyridinium-1-yl, tri(C$_1$–C$_4$)alkylammonium-N-yl, 1-methylpiperidinium-1-yl, and 1,4-dimethylpiperazinium-1-yl groups.

23. The cationic 2-acylaminophenol of claim 20, wherein $R_4$ of formula (II) is chosen from hydrogen and chlorine atoms; a group Z; methyl, ethyl, hydroxymethyl, methoxymethyl, aminomethyl, methylaminomethyl, hydroxyl, methoxy, acetoxy, amino, methylamino, N-piperidino, and N-morpholino groups; —NH(CO)$R_{15}$ groups, wherein $R_{15}$ is chosen from a group (G1); and —NHSO$_2$R$_{16}$ groups, wherein $R_{16}$ is chosen from a group (G3), wherein:

said group (G1) is chosen from methyl, ethyl, propyl, isopropyl, butyl, isobutyl, tert-butyl, pentyl, isopentyl, neopentyl, hexyl, cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl, phenyl, methylphenyl, dimethylphenyl, 2,4, 6-trimethylphenyl, 4-ethylphenyl, (trifluoromethyl) phenyl, hydroxyphenyl, methoxyphenyl, ethoxyphenyl, acetoxyphenyl, (trifluoromethoxy) phenyl, aminophenyl, 4-dimethylaminophenyl, fluorophenyl, difluorophenyl, fluoro(trifluoromethyl) phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl, tetrahydrofur-2-yl, fur-2-yl, 5-methyl-2-(trifluoromethyl)fur-3-yl, 2-methyl-5-phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tertbutyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy) ethyl, 1-phenoxyethyl, 1-acetoxyethyl, methoxycarbonyl, ethoxycarbonyl, (methoxycarbonyl) methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy, amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl) phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl, and 4-morpholinyl groups; and said group (G3) is chosen from methyl, trifluoromethyl, ethyl, 2-chloroethyl, propyl, 3-chloropropyl, isopropyl, butyl, thien-2-yl, hydroxyl, ethoxy, and dimethylamino groups.

24. The cationic 2-acylaminophenol of claim 11, wherein $R_4$ in formula (II) is chosen from hydrogen and chlorine atoms; methyl, hydroxymethyl, aminomethyl, hydroxyl, methoxy, amino, and methylamino groups; a methanesulphonylamino group; an ethanesulphonylamino group; a dimethylaminosulphonylamino group; —NH(CO)$R_{17}$ groups, wherein $R_{17}$ is chosen from a group (G2); and —O—E—$D_3$, —NH—E—$D_3$, —NH(CO)—$D_3$, —NH(CO)—E—$D_3$, —NH(CO)O—E—$D_3$, —NH(CO)NH—E—$D_3$, and —NH(SO$_2$)—E—$D_3$ groups, wherein:

said group (G2) is chosen from methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl, and 4-morpholinyl groups;

—E— is chosen from —(CH$_2$)$_q$— groups, q being an integer having a value chosen from 1 and 2; and $D_3$ is chosen from a group D', wherein group D' is chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C$_1$–C$_4$)alkylpyridinium-2-yl, N—(C$_1$–C$_4$)alkylpyridinium-3-yl, N—(C$_1$–C$_4$)alkylpyridinium-4-yl, N-(2-hydroxyethyl)pyridinium-2-yl, N-(2-hydroxyethyl) pyridinium-3-yl, N-(2-hydroxyethyl)pyridinium-4-yl, pyridinium-1-yl, tri(C$_1$–C$_4$)alkylammonium-N-yl, 1-methylpiperidinium-1-yl, and 1,4-dimethylpiperazinium-1-yl groups.

25. The cationic 2-acylaminophenol of claim 11, wherein $R_5$ is chosen from hydrogen and halogen atoms; group Z; and $A_1$, $A_2$, $A_3$, $A_4$, and $A_5$ groups optionally separated from the phenolic nucleus of the compounds of formula (II) by group chosen from oxygen and sulphur atoms, and —NH—, —N(C$_1$–C$_3$)alkyl-NH(CO)—, —N(C$_1$–C$_3$)alkyl(CO)—, —NH[C=NH]—, —NH(CO)NH—, —NH(CO)N(C$_1$–C$_3$) alkyl-, and —NH(CO)O— groups, wherein:

$A_1$ is chosen from linear and branched $C_1$–$C_8$ alkyl radicals,
wherein said linear and branched $C_1$–$C_8$ alkyl radicals may comprise one double bond, two double bonds, or one triple bond,
said linear and branched $C_1$–$C_8$ alkyl radicals may be unsubstituted or substituted with at least one substituent chosen from group $A_2$, group $A_4$, and group $A_5$; said linear and branched $C_1$–$C_8$ alkyl radicals may be substituted with one or two groups, which may be identical or different, chosen from N—(C$_1$–C$_3$)alkylamino, N—(C$_1$–C$_3$)alkyl-N—(C$_1$–C$_3$)alkylamino, (C$_1$–C$_6$)alkoxy, oxo, alkoxycarbonyl, acyloxy, amide, acylamino, ureyl, sulphoxy, sulphonyl, sulphonamido, sulphonylamino, bromo, cyano, and carboxyl groups; and said linear and branched $C_1$–$C_8$ alkyl radicals may be substituted with at least one substituent chosen from hydroxyl, fluoro, and chloro groups, $A_2$ is chosen from aromatic groups, wherein said aromatic groups may be unsubstituted or substituted with one to three groups, which may be identical or different, chosen from methyl, trifluoromethyl, ethyl, isopropyl, butyl, pentyl, fluoro, chloro, bromo, methoxy, trifluoromethoxy, ethoxy, propyloxy, acetyloxy, acetyl, and cyano groups, $A_3$ is chosen from heteroaromatic groups chosen from furyl, thienyl, pyrrolyl, imidazolyl, thiazolyl, oxazolyl, 1,2,3-triazolyl, 1,2,4-triazolyl, isoxazolyl, isothiazolyl, pyrazolyl, pyrazolotriazolyl, pyrazoloimidazolyl, pyrrolotriazolyl, pyrazolopyrimidyl, pyrazolopyridyl, pyridyl, pyrimidyl, benzimidazolyl, benzoxazolyl, benzothiazolyl, indolyl, indolidinyl, isoindolyl, indazolyl, benzotriazolyl, quinolyl, benzimidazolyl, and benzopyrimidyl groups, wherein
said heteroaromatic groups are unsubstituted or substituted with from 1 to 3 substituents, which may be identical or different, chosen from linear and branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino, and hydroxyl groups, $A_4$ is chosen from $C_3$–$C_7$ cycloalkyl groups, and norbornanyl radicals, wherein said norbornanyl radicals may comprise a double bond, and may be unsubstituted or substituted with from 1 to 2 substituents, which may be the same or different, chosen from linear and branched $C_1$–$C_4$ alkyl, $C_1$–$C_4$ monohydroxyalkyl, $C_2$–$C_4$ polyhydroxyalkyl, carboxyl, alkoxycarbonyl, halogen, amido, amino, and hydroxyl radicals, and $A_5$ is chosen from heterocycles chosen from dihydrofuryl, tetrahydrofuryl, butyrolactonyl, dihydrothienyl, tetrahydrothienyl, tetrahydrothienonyl, iminothiolane, dihydropyrrolyl, pyrrolidinyl, pyrrolidinonyl, imidazolidinonyl, imidazolidinothienyl, oxazolidinyl, oxazolidinonyl, oxazolanethione, thiazolidinyl, isothiazolonyl, mercaptothiazolinyl, pyrazolidinonyl, iminothiolane, dioxolanyl, pentalactone, dioxanyl, dihydropyridyl, piperidyl, pentalactam, morpholinyl, pyrazoli(di)nyl, pyrimi(di)nyl, pyrazinyl, piperazinyl, and azepinyl rings.

26. The cationic 2-acylaminophenol of claim 11, wherein $R_5$ in formula (II) is chosen from hydrogen, chlorine, fluorine, and bromine atoms; group Z; methyl, trifluoromethyl, allyl, methoxy, and methylamino groups; and —NH(CO)$R_{18}$ groups, wherein $R_{18}$ is chosen from group (G1), wherein:

said group (G1) is chosen from methyl, ethyl, propyl, isopropyl, butyl, isobutyl, tert-butyl, pentyl, isopentyl, neopentyl, hexyl, cyclopropyl, cyclobutyl, cyclopentyl, cyclopentylmethyl, 3-cyclopentylpropyl, cyclohexyl, 2-cyclohexylethyl, norbornan-2-yl, vinyl, 1-methylvinyl, 2-methylvinyl, 2,2-dimethylvinyl, allyl, 3-butenyl, phenyl, methylphenyl, dimethylphenyl, 2,4,6-trimethylphenyl, 4-ethylphenyl, (trifluoromethyl)phenyl, hydroxyphenyl, methoxyphenyl, ethoxyphenyl, acetoxyphenyl, (trifluoromethoxy)phenyl, aminophenyl, 4-dimethylaminophenyl, fluorophenyl, difluorophenyl, fluoro(trifluoromethyl)phenyl, chlorophenyl, dichlorophenyl, bromophenyl, 1-naphthyl, 2-naphthyl, (2-methoxy)naphth-1-yl, benzyl, 4'-methoxybenzyl, 2',5'-dimethoxybenzyl, 3',4'-dimethoxybenzyl, 4'-fluorobenzyl, 4'-chlorobenzyl, phenethyl, 2-phenylvinyl, (1-naphthyl)methyl, (2-naphthyl)methyl, tetrahydrofur-2-yl, fur-2-yl, 5-methyl-2-(trifluoromethyl)fur-3-yl, 2-methyl-5-phenylfur-3-yl, thien-2-yl, (thien-2-yl)methyl, 3-chlorothien-2-yl, 2,5-dichlorothien-3-yl, benzothien-2-yl, 3-chlorobenzothien-2-yl, isoxazol-5-yl, 5-methylisoxazol-3-yl, 3,5-dimethylisoxazol-4-yl, 1,3-dimethylpyrazol-5-yl, 1-ethyl-3-methylpyrazol-5-yl, 1-tert-butyl-3-methylpyrazol-5-yl, 3-tertbutyl-1-methylpyrazol-5-yl, 4-bromo-1-ethyl-3-methylpyrazol-5-yl, indol-3-ylcarboxyl, pyridyl, chloropyridyl, dichloropyridyl, 5-(bromo)pyrid-3-yl, piperazin-2-yl, quinoxal-2-yl, fluoromethyl, difluoromethyl, trifluoromethyl, 1,1,2,2-tetrafluoroethyl, pentafluoroethyl, heptafluoropropyl, 1,1,2,2,3,3,4,4-octafluorobutyl, nonafluorobutyl, chloromethyl, chloroethyl, 1,1-dimethyl-2-chloroethyl, 1,2-dichloroethyl, 1-chloropropyl, 3-chloropropyl, 4-chlorobutyl, hydroxymethyl, methoxymethyl, phenoxymethyl, (4-chlorophenoxy)methyl, benzyloxymethyl, acetoxymethyl, 1,2-dihydroxyethyl, 1-phenoxyethyl, 1-acetoxyethyl, 2-(2-carboxyethoxy)ethyl, 1-phenoxyethyl, 1-acetoxyethyl, methoxycarbonyl, ethoxycarbonyl, (methoxycarbonyl)methyl, 2-carboxyethyl, 2-(methoxycarbonyl)ethyl, 2-carboxycyclopropyl, 2-carboxycyclohexane, methoxy, ethoxy, propoxy, isopropoxy, butoxy, isobutoxy, pentoxy, neopentoxy, hexyloxy, cyclopentyloxy, cyclohexyloxy, vinyloxy, allyloxy, propargyloxy, chloromethoxy, 1-chloroethoxy, 2-methoxyethoxy, 4-chlorobutoxy, phenoxy, 4-methylphenoxy, 4-fluorophenoxy, 4-bromophenoxy, 4-chlorophenoxy, 4-methoxyphenoxy, naphth-2-yloxy, benzyloxy, amino, methylamino, ethylamino, propylamino, isopropylamino, butylamino, cyclohexylamino, allylamino, 2-chloroethylamino, 3-chloropropylamino, carboxymethylamino, phenylamino, fluorophenylamino, (trifluoromethyl)phenylamino, chlorophenylamino, bromophenylamino, 4-acetylphenylamino, methoxyphenylamino, (trifluoromethoxy)phenylamino, naphth-1-ylamino, benzylamino, phenethylamino, pyrid-3-ylamino, dimethylamino, 1-pyrrolidinyl, and 4-morpholinyl groups.

27. The cationic 2-acylaminophenol of claim 11, wherein $R_5$ in formula (II) is chosen from hydrogen, chlorine, and fluorine atoms; methyl, methoxy, and methylamino groups; —NH(CO)$R_{19}$ groups, wherein $R_{19}$ is chosen from a group (G2); and —O—E—$D_4$, —NH—E—$D_4$, —NH(CO)—$D_4$, —NH(CO)—E—$D_4$, —NH(CO)O—E—$D_4$, and —NH(CO)NH—E—$D_4$ groups, wherein:

said group (G2) is chosen from methyl, ethyl, propyl, allyl, phenyl, tetrahydrofur-2-yl, fur-2-yl, thien-2-yl, pyridyl, piperazin-2-yl, fluoromethyl, chloromethyl, 2-chloroethyl, methoxymethyl, acetoxymethyl, 1,2-dihydroxyethyl, methoxycarbonyl, 2-carboxyethyl, methoxy, ethoxy, propoxy, allyloxy, 2-chloroethoxy, 2-methoxyethoxy, amino, ethylamino, allylamino, 2-chloroethylamino, pyridylamino, dimethylamino, 1-pyrrolidinyl, and 4-morpholinyl groups;

—E— is chosen from —(CH$_2$)$_q$— groups, q being an integer having a value chosen from 1 and 2; and $D_4$ is chosen from a group D', wherein group D' is chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C$_1$–C$_4$)alkylpyridinium-2-yl, N—(C$_1$–C$_4$)alkylpyridinium-3-yl, N—(C$_1$–C$_4$)alkylpyridinium-4-yl, N-(2-hydroxyethyl)pyridinium-2-yl, N-(2-hydroxyethyl)pyridinium-3-yl, N-(2-hydroxyethyl)pyridinium-4-yl, pyridinium-1-yl, tri(C$_1$–C$_4$)alkylammonium-N-yl, 1-methylpiperidinium-1-yl, and 1,4-dimethylpiperazinium-1-yl groups.

28. The cationic 2-acylaminophenol of claim 11, wherein Y in formula (II) is chosen from hydrogen, chlorine, fluorine, and bromine atoms; methoxy, ethoxy, propoxy, benzyloxy, and phenoxy groups; and —OCH$_2$CH$_2$OCH$_3$, —OCH$_2$CH$_2$OCH$_3$, —OCH$_2$CH$_2$N(CH$_3$)$_2$, —OCH$_2$(CO)OH, —OCH$_2$(CO)OCH$_3$, —OCH$_2$(CO)OC$_2$H$_5$, —SCH$_2$CH$_2$CO$_2$H, and —NHSO$_2$CH$_3$ groups, with the proviso that Y is not chosen from —NHSO$_2$CH$_3$ when $R_3$ is chosen from a hydroxyl group.

29. The cationic 2-acylaminophenol of claim 11, wherein D in formula (IV) is chosen from imidazolinium, thiazolinium, oxazolinium, pyrrolinium, 1,2,3-triazolinium, 1,2,4-triazolinium, isoxazolinium, isothiazolinium, imidazolidinium, thiazolidinium, pyrazolinium, pyrazolidinium, oxazolidinium, pyrazolotriazolinium, pyrazoloimidazolinium, pyrrolotriazolinium, pyrazolopyrimidinium, pyrazolopyridinium, pyridinium, pyrimidinium, pyrazinium, triazinium, benzoimidazolinium, benzoxazolinium, benzothiazolinium, indolinium, indolidinium, isoindolinium, indazolinium, benzotriazolinium, quinolinium, tetrahydroquinolinium, benzoimidazolidinium, benzopyrimidinium, (C$_1$–C$_4$) tetraalkylammonium, polyhydroxy(C$_1$–C$_4$) tetraalkylammonium, dialkylpiperidinium, dialkylpyrrolidinium, dialkylmorpholinium, dialkylthiomorpholinium, dialkylpiperazinium, azepinium, and 1,4-diazabicyclo[2,2,2]octanium groups.

30. The cationic 2-acylaminophenol of claim 29, wherein D in formula (IV) is chosen from 3-methylimidazolidinium-1-yl, 3-(2-hydroxyethyl)imidazolidinium-1-yl, 1,2,4-triazolinium-1-yl, 1,2,4-triazolinium-4-yl, N—(C$_1$–C$_4$)alkylpyridinium-2-yl, N—(C$_1$–C$_4$)alkylpyridinium-3-yl, N—(C$_1$–C$_4$)alkylpyridinium-4-yl, N-(2-hydroxyethyl)pyridinium-2-yl, N-(2-hydroxyethyl)pyridinium-3-yl, N-(2-hydroxyethyl)pyridinium-4-yl, pyridinium-1-yl, (C$_1$–C$_4$)trialkylammonium-N-yl, 1-methylpiperidinium-1-yl, and 1,4-dimethylpiperazinium-1-yl groups.

31. The cationic 2-acylaminophenol of claim 11, wherein A is chosen from imidazolidinium, N—(C$_1$–C$_4$)alkylpyridinium, N-(2-hydroxyethyl)pyridinium, pyridinium, di(C$_1$–C$_4$)alkylammonium, and 1,4-dimethylpiperazinium-1-yl groups.

32. The cationic 2-acylaminophenol of claim 11, wherein B, $B_1$, and $B_2$, independently, are each chosen from —(CH$_2$)—, —(CH$_2$)—(CH$_2$)—, and —(CH$_2$)—(CH$_2$)—(CH$_2$)— groups.

33. A compound chosen from:

1,3-bis[(2-hydroxyphenylcarbamoyl)methyl]-3H-imidazol-1-ium chloride;
1,3-bis[(2-hydroxy-4-methylphenylcarbamoyl)methyl]-3H-imidazol-1-ium chloride;
1,3-bis[(2-hydroxy-4-aminophenylcarbamoyl)methyl]-3H-imidazol-1-ium chloride;
1,3-bis[(2-hydroxy-4-acetylaminophenylcarbamoyl)methyl]-3H-imidazol-1-ium chloride;
1,3-bis[(2-hydroxy-4-methoxycarbonylaminophenylcarbamoyl)methyl]-3H-imidazol-1-ium chloride;
1,3-bis[(3-hydroxy-4-acetylaminophenylcarbamoyl)methyl]-3H-imidazol-1-ium chloride;
1,3-bis[(3-hydroxy-4-methoxycarbonylaminophenylcarbamoyl)methyl]-3H-imidazol-1-ium chloride;
1,3-bis[(2-hydroxy-5-chlorophenylcarbamoyl)methyl]-3H-imidazol-1-ium chloride;
1,3-bis[(2-hydroxy-4-methyl-5-chlorophenylcarbamoyl)methyl]-3H-imidazol-1-ium chloride;
1,3-bis[(2-hydroxy-4-amino-5-chlorophenylcarbamoyl)methyl]-3H-imidazol-1-ium chloride;
1,3-bis[(2-hydroxy-4-acetylamino-5-chlorophenylcarbamoyl)methyl]-3H-imidazol-1-ium chloride;
1,3-bis[(2-hydroxy-4-methoxycarbonylamino-5-chlorophenylcarbamoyl)methyl]-3H-imidazol-1-ium chloride;
1,3-bis[(3-hydroxy-4-acetylamino-5-chlorophenylcarbamoyl)methyl]-3H-imidazol-1-ium chloride;
1,3-bis[(3-hydroxy-4-methoxycarbonylamino-6-chlorophenylcarbamoyl)methyl]-3H-imidazol-1-ium chloride;
1,3-bis[(2-hydroxy-5-methoxyphenylcarbamoyl)methyl]-3H-imidazol-1-ium chloride;
1,3-bis[(2-hydroxy-4-methyl-5-methoxyphenylcarbamoyl)methyl]-3H-imidazol-1-ium chloride;
1,3-bis[(2-hydroxy-4-amino-5-methoxyphenylcarbamoyl)methyl]-3H-imidazol-1-ium chloride;
1,3-bis[(2-hydroxy-4-acetylamino-5-methoxyphenylcarbamoyl)methyl]-3H-imidazol-1-ium chloride;
1,3-bis[(2-hydroxy-4-methoxycarbonylamino-5-methoxyphenylcarbamoyl)methyl]-3H-imidazol-1-ium chloride;
1,3-bis[(3-hydroxy-4-acetylamino-6-methoxyphenylcarbamoyl)methyl]-3H-imidazol-1-ium chloride;
1,3-bis[(3-hydroxy-4-methoxycarbonylamino-6-methoxyphenylcarbamoyl)methyl]-3H-imidazol-1-ium chloride;
1,3-bis[(2-hydroxy-6-aminophenylcarbamoyl)methyl]-3H-imidazol-1-ium chloride;
1,3-bis[(2-hydroxy-6-acetylaminophenylcarbamoyl)methyl]-3H-imidazol-1-ium chloride;
1,3-bis[(2-hydroxy-4,6-diaminophenylcarbamoyl)methyl]-3H-imidazol-1-ium chloride;
1,3-bis[(2-hydroxy-4-acetylamino-6-aminophenylcarbamoyl)methyl]-3H-imidazol-1-ium chloride;
1,3-bis[(2-hydroxy-3,5-dichloro-4-methylphenylcarbamoyl)methyl]-3H-imidazol-1-ium chloride;
1,3-bis[(2-hydroxy-3,5-dichloro-4-aminophenylcarbamoyl)methyl]-3H-imidazol-1-ium chloride;
1,3-bis[(2-hydroxy-3,5-dichloro-4-acetylaminophenylcarbamoyl)methyl]-3H-imidazol-1-ium chloride;
1,3-bis[(2-hydroxy-3,5-dichloro-4-methoxycarbonylaminophenylcarbamoyl)methyl]-3H-imidazol-1-ium chloride;
1,3-bis[(2-hydroxy-3-acetylaminophenylcarbamoyl)methyl]-3H-imidazol-1-ium chloride;
3-[(2-hydroxy-4-aminophenylcarbamoyl)methyl]-1-[(2-hydroxy-4-methylphenylcarbamoyl)methyl]-3H-imidazol-1-ium chloride;
3-[(2-hydroxy-3,5-dichloro-4-methylphenylcarbamoyl)methyl]-1-[(2-hydroxy-4-methylphenylcarbamoyl)methyl]-3H-imidazol-1-ium chloride;
1,4-bis[(2-hydroxyphenylcarbamoyl)methyl]-1-methylpiperazin-1-ium chloride;
1,4-bis[(2-hydroxy-4-methylphenylcarbamoyl)methyl]-1-methylpiperazin-1-ium chloride;
1,4-bis[(2-hydroxy-4-aminophenylcarbamoyl)methyl]-1-methylpiperazin-1-ium chloride;
1,4-bis[(2-hydroxy-4-acetylaminophenylcarbamoyl)methyl]-1-methylpiperazin-1-ium chloride;
1,4-bis[(2-hydroxy-4-methoxycarbonylaminophenylcarbamoyl)methyl]-1-methylpiperazin-1-ium chloride;
1,4-bis[(3-hydroxy-4-acetylaminophenylcarbamoyl)methyl]-1-methylpiperazin-1-ium chloride;
1,4-bis[(3-hydroxy-4-methoxycarbonylaminophenylcarbamoyl)methyl]-1-methylpiperazin-1-ium chloride;
1,4-bis[(2-hydroxy-5-chlorophenylcarbamoyl)methyl]-1-methylpiperazin-1-ium chloride;
1,4-bis[(2-hydroxy-4-methyl-5-chlorophenylcarbamoyl)methyl]-1-methylpiperazin-1-ium chloride;
1,4-bis[(2-hydroxy-4-amino-5-chlorophenylcarbamoyl)methyl]-1-methylpiperazin-1-ium chloride;
1,4-bis[(2-hydroxy-4-acetylamino-5-chlorophenylcarbamoyl)methyl]-1-methylpiperazin-1-ium chloride;
1,4-bis[(2-hydroxy-4-methoxycarbonylamino-5-chlorophenylcarbamoyl)methyl]-1-methylpiperazin-1-ium chloride;
1,4-bis[(3-hydroxy-4-acetylamino-6-chlorophenylcarbamoyl)methyl]-1-methylpiperazin-1-ium chloride;
1,4-bis[(3-hydroxy-4-methoxycarbonylamino-6-chlorophenylcarbamoyl)methyl]-1-methylpiperazin-1-ium chloride;
1,4-bis[(2-hydroxy-5-methoxyphenylcarbamoyl)methyl]-1-methylpiperazin-1-ium chloride;
1,4-bis[(2-hydroxy-4-methyl-5-methoxyphenylcarbamoyl)methyl]-1-methylpiperazin-1-ium chloride;
1,4-bis[(2-hydroxy-4-amino-5-methoxyphenylcarbamoyl)methyl]-1-methylpiperazin-1-ium chloride;
1,4-bis[(2-hydroxy-4-acetylamino-5-methoxyphenylcarbamoyl)methyl]-1-methylpiperazin-1-ium chloride;
1,4-bis[(2-hydroxy-4-methoxycarbonylamino-5-methoxyphenylcarbamoyl)methyl]-1-methylpiperazin-1-ium chloride;
1,4-bis[(3-hydroxy-4-acetylamino-6-methoxyphenylcarbamoyl)methyl]-1-methylpiperazin-1-ium chloride;
1,4-bis[(3-hydroxy-4-methoxycarbonylamino-6-methoxyphenylcarbamoyl)methyl]-1-methylpiperazin-1-ium chloride;

1,4-bis[(2-hydroxy-6-aminophenylcarbamoyl)methyl]-1-methylpiperazin-1-ium chloride;

1,4-bis[(2-hydroxy-6-acetylaminophenylcarbamoyl)methyl]-1-methylpiperazin-1-ium chloride;

1,4-bis[(2-hydroxy-4,6-diaminophenylcarbamoyl)methyl]-1-methylpiperazin-1-ium chloride;

1,4-bis[(2-hydroxy-4-acetylamino-6-aminophenylcarbamoyl)methyl]-1-methylpiperazin-1-ium chloride;

1,4-bis[(2-hydroxy-3,5-dichloro-4-methylphenylcarbamoyl)methyl]-1-methylpiperazin-1-ium chloride;

1,4-bis[(2-hydroxy-3,5-dichloro-4-aminophenylcarbamoyl)methyl]-1-methylpiperazin-1-ium chloride;

1,4-bis[(2-hydroxy-3,5-dichloro-4-acetylaminophenylcarbamoyl)methyl]-1-methylpiperazin-1-ium chloride;

1,4-bis[(2-hydroxy-3,5-dichloro-4-methoxycarbonylaminophenylcarbamoyl)methyl]-1-methylpiperazin-1-ium chloride;

1,4-bis[(2-hydroxy-3-acetylaminophenylcarbamoyl)methyl]-1-methylpiperazin-1-ium chloride; and acid addition salts thereof.

34. The cationic 2-acylaminophenol of claim 11, wherein the acid addition salt is chosen from hydrochlorides, hydrobromides, sulphates, citrates, succinates, tartrates, lactates, and acetates.

* * * * *

UNITED STATES PATENT AND TRADEMARK OFFICE
CERTIFICATE OF CORRECTION

PATENT NO. : 6,455,737 B1
DATED : September 24, 2002
INVENTOR(S) : Laurent Vidal et al.

It is certified that error appears in the above-identified patent and that said Letters Patent is hereby corrected as shown below:

<u>Title page,</u>
Item [54], the title should read -- CATIONIC 2-ACYLAMINOPHENOLS, THEIR USE AS COUPLERS FOR OXIDATION DYEING, COMPOSITIONS CONTAINING THEM, AND DYEING METHODS --.

<u>Column 20,</u>
Line 65, "R1" should read -- $R_1$ --.

<u>Column 29,</u>
Line 39, insert "$W_1$" before -- directly --.

<u>Column 43,</u>
Line 57, "$C_1$-$C_8$" should read -- $C_1$-$C_8$ --.

Signed and Sealed this

Eighteenth Day of March, 2003

JAMES E. ROGAN
*Director of the United States Patent and Trademark Office*